(12) United States Patent
Ramdahl

(10) Patent No.: US 10,682,430 B2
(45) Date of Patent: *Jun. 16, 2020

(54) ALPHA-EMITTING COMPLEXES

(71) Applicant: BAYER AS, Drammensveien (NO)

(72) Inventor: Thomas Ramdahl, Eiksmarka (NO)

(73) Assignee: BAYER AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 15/629,409

(22) Filed: Jun. 21, 2017

(65) Prior Publication Data

US 2017/0319721 A1    Nov. 9, 2017

Related U.S. Application Data

(63) Continuation of application No. 13/578,578, filed as application No. PCT/EP2011/052158 on Feb. 14, 2011, now Pat. No. 9,724,436.

(30) Foreign Application Priority Data

Feb. 12, 2010 (GB) .................................. 1002508.8

(51) Int. Cl.
| | |
|---|---|
| *A61K 51/00* | (2006.01) |
| *A61K 51/04* | (2006.01) |
| *A61K 51/10* | (2006.01) |
| *A61P 35/00* | (2006.01) |

(52) U.S. Cl.
CPC ...... *A61K 51/0478* (2013.01); *A61K 51/1045* (2013.01); *A61K 51/1051* (2013.01); *A61K 51/1072* (2013.01); *A61K 51/1093* (2013.01); *A61P 35/00* (2018.01)

(58) Field of Classification Search
CPC ............ A61K 2121/00; A61K 2123/00; A61K 51/00; A61K 38/00; A61K 51/0478; A61K 51/1072; A61K 51/1051; A61K 51/1045; A61K 51/1093; A61K 35/00; C07D 213/02; C07D 211/06; C07D 295/00
USPC .... 424/1.11, 1.49, 1.65, 1.69, 1.73, 9.1, 9.3, 424/9.4, 9.5; 514/1, 1.1; 534/10, 11, 12; 546/1, 184, 255
See application file for complete search history.

(56) References Cited

U.S. PATENT DOCUMENTS

| | | | |
|---|---|---|---|
| 5,428,154 | A | 6/1995 | Gansow et al. |
| 5,892,029 | A | 4/1999 | Raymond |
| 6,083,477 | A | 7/2000 | Goldenberg |
| 6,153,596 | A | 11/2000 | Liotta et al. |
| 6,592,843 | B2 | 7/2003 | Larsen et al. |
| 6,635,234 | B1 | 10/2003 | Larsen et al. |
| 6,740,304 | B2 | 5/2004 | Larsen et al. |
| 7,056,275 | B2 | 6/2006 | Larsen et al. |
| 7,144,991 | B2 | 12/2006 | Goshorn et al. |
| 7,335,154 | B2 | 2/2008 | Larsen et al. |
| 8,142,758 | B2 | 3/2012 | Larsen et al. |
| 8,926,943 | B2 | 1/2015 | Karlson et al. |
| 9,056,142 | B2 | 6/2015 | Karlson et al. |
| 9,724,436 | B2 * | 8/2017 | Ramdahl ............ A61K 51/0478 |
| 9,827,336 | B2 * | 11/2017 | Bonge-Hansen ........................... A61K 51/0478 |
| 2001/0008625 | A1 | 7/2001 | Larsen et al. |
| 2001/0048914 | A1 | 12/2001 | Larsen et al. |
| 2003/0086868 | A1 | 5/2003 | Ma et al. |
| 2003/0166989 | A1 | 9/2003 | Larsen |
| 2003/0206857 | A1 | 11/2003 | Larsen et al. |
| 2003/0228256 | A1 | 12/2003 | Inverardi et al. |
| 2004/0009955 | A1 | 1/2004 | Larsen et al. |
| 2004/0184990 | A1 | 9/2004 | Larsen et al. |
| 2004/0208821 | A1 * | 10/2004 | Larsen ............... A61K 51/1027 424/1.11 |
| 2006/0135842 | A1 | 6/2006 | Larsen et al. |
| 2006/0228297 | A1 | 10/2006 | Larsen et al. |
| 2008/0193374 | A1 | 8/2008 | Larsen et al. |
| 2011/0189088 | A1 * | 8/2011 | Xu ....................... C07D 213/89 424/1.73 |
| 2014/0235924 | A1 | 8/2014 | Larsen et al. |
| 2015/0104385 | A1 | 4/2015 | Bonge-Hansen et al. |
| 2015/0104386 | A1 | 4/2015 | Karlson et al. |
| 2015/0110817 | A1 | 4/2015 | Bonge-Hansen et al. |
| 2015/0147272 | A1 | 5/2015 | Bonge-Hansen et al. |
| 2015/0258223 | A1 | 9/2015 | Larsen et al. |
| 2015/0306257 | A1 | 10/2015 | Ramdahl |

FOREIGN PATENT DOCUMENTS

| | | |
|---|---|---|
| WO | WO-90/15625 A1 | 12/1990 |
| WO | WO-93/20852 A2 | 10/1993 |
| WO | WO-00/52031 A2 | 9/2000 |
| WO | WO-01/39806 A1 | 6/2001 |

(Continued)

OTHER PUBLICATIONS

International Search Report and Written Opinion of the International Searching Authority for Application No. PCT/EP2011/052158 dated Jun. 9, 2011. (11 pages).
Reply to Written Opinion of the International Preliminary Examining Authority for Application No. PCT/EP2011/052158 dated May 23, 2012. (5 pages).
International Preliminary Report on Patentability for PCT/EP2011/052158, dated Jun. 25, 2012. (6 pages).
Abbatt, "History of the use and toxicity of thorotrast," Environ Res. 18(1):6-12 (1979).
Charlton et al., "Theoretical treatment of human haemopoietic stem cell survival following irradiation by alpha particles," Int J Radiat Biol. 74(1):111-8 (1998).

(Continued)

*Primary Examiner* — D. L. Jones
(74) *Attorney, Agent, or Firm* — Morrison & Foerster LLP

(57) ABSTRACT

The present invention provides a tissue-targeting complex comprising a tissue targeting moiety, an octadentate hydroxypyridinone-containing ligand and the ion of an alpha-emitting thorium radionuclide. The invention additionally provides therapeutic methods employing such complexes, methods of their production and use, and kits and pharmaceutical compositions comprising such complexes.

4 Claims, 20 Drawing Sheets

(56) References Cited

FOREIGN PATENT DOCUMENTS

| WO | WO-01/60417 A2 | 8/2001 |
|---|---|---|
| WO | WO-01/66155 A2 | 9/2001 |
| WO | WO-02/05859 A2 | 1/2002 |
| WO | WO-2004/043487 A1 | 5/2004 |
| WO | WO 2004/091668 A1 | 10/2004 |
| WO | WO 2006/003123 A2 | 1/2006 |
| WO | WO 2011/098611 A2 | 8/2011 |

OTHER PUBLICATIONS

Dahle et al., "Targeted cancer therapy with a novel low-dose rate alpha-emitting radioimmunoconjugate," Blood. 110(6):2049-56 (2007).
Deal et al., "Improved in vivo stability of actinium-225 macrocyclic complexes," J Med Chem. 42(15):2988-92 (1999).
Feinendegen et al., "Alpha-Emitters for Medical Therapy-Workshop of the United States Department of Energy," Radiat Res. 148:195-201 (1997).
Geerlings et al., "The feasibility of 225Ac as a source of alpha-particles in radioimmunotherapy," Nucl Med Commun. 14(2):121-5 (1993).
Henriksen et al., "Evaluation of potential chelating agents for radium," Appl Radiat Isot. 56(5):667-71 (2002).
Horak et al., "Radioimmunotherapy targeting of HER2/neu oncoprotein on ovarian tumor using lead-212-DOTA-AE1," J Nucl Med. 38(12):1944-50 (1997).
Jacques et al., "Kinetically and thermodynamically stable isomers of thorium chelates of polyaza polycarboxylic macrocycles," J Alloys Compd. 213-214:286-289 (1994) (Abstract Only).
Kennel et al., "Evaluation of 225Ac for vascular targeted radioimmunotherapy of lung tumors," Cancer Biother Radiopharm. 15(3):235-44 (2000).
Kolbert et al., "Parametric images of antibody pharmacokinetics in Bi213-HuM195 therapy of leukemia," J Nucl Med. 42(1):27-32 (2001).
Kozak et al., "Bismuth-212-labeled anti-Tac monoclonal antibody: alpha-particle-emitting radionuclides as modalities for radioimmunotherapy," Proc Natl Acad Sci USA. 83(2):474-8 (1986).
Larsen et al., "Treatment of Skeletal Metastases with Alpha Emitting 223Ra: Blood Clearance Pattern in Patients with Advanced Breast and Prostate Cancer," J Nucl Med. 43(5, Supplement):160P (2002) (Abstract 580).
Larsen et al., "Alpha-particle radiotherapy with 211At-labeled monodisperse polymer particles, 211At-labeled IgG proteins, and free 211At in a murine intraperitoneal tumor model," Gynecol Oncol. 57(1):9-15 (1995).
Mausner et al., "Selection of radionuclides for radioimmunotherapy," Med Phys. 20 (2 Pt 2):503-9 (1993).
McClure et al., *Alpha Emitters for Medical Therapy: Second Bi-Annual Workshop*. Toronto, Canada, Jun. 4-5, 1998. DOE/NE-0116, U.S. Department of Energy, 1-25 (1998).
McDevitt et al., "Tumor therapy with targeted atomic nanogenerators," Science. 294(5546):1537-40 (2001).
Milenic et al., "In vivo comparison of macrocyclic and acyclic ligands for radiolabeling of monoclonal antibodies with 177Lu for radioimmunotherapeutic applications," Nucl Med Biol. 29(4):431-42 (2002).
Muggenburg et al., "The biological effects of radium-224 injected into dogs," Radiat Res. 146(2):171-86 (1996).
Müller, "Studies on short-lived internal alpha-emitters in mice and rats. II. 227Th," Int J Radiat Biol. 20(3):233-43 (1971).
Müller et al., "Metabolic and dosimetric studies after inhalation of 227Th in rats with regard to the risk of lung and bone tumors," Radiat Environ Biophys. 11(4):309-18 (1975).
McDevitt et al., "Tumor therapy with targeted atomic nanogenerators: Supplementary material," Science. 294(5546):1537-40 (2001).
Wilbur, "Potential Use of Alpha Emitting Radionuclides in the Treatment of Cancer," Antibody, Immunoconjugates, and Radiopharmaceuticals 4(1):85-97 (1991).
Zalutsky et al., "High-level production of alpha-particle-emitting 211At and preparation of 211At-labeled antibodies for clinical use," J Nucl Med. 42(10):1508-15 (2001).

\* cited by examiner

ALPHA-EMITTING COMPLEXES

CROSS REFERENCE

This application is a continuation of U.S. patent application Ser. No. 13/578,578, filed Mar. 27, 2013, allowed, which is the U.S. National Phase of International Application No. PCT/EP2011/052158 filed Feb. 14, 2011 which designates the U.S. and claims priority to Great Britain Patent Application No. 1002508.8 filed Feb. 12, 2010, the entire contents of each of which are hereby incorporated by reference.

FIELD OF THE INVENTION

The present invention relates to complexes of thorium isotopes and particularly with complexes of thorium-227 with certain octadentate ligands. The invention also relates to the treatment of disease, particularly neoplastic diseases, involving the administration of such complexes.

BACKGROUND TO THE INVENTION

Specific cell killing can be essential for the successful treatment of a variety of diseases in mammalian subjects. Typical examples of this are in the treatment of malignant diseases such as sarcomas and carcinomas. However the selective elimination of certain cell types can also play a key role in the treatment of other diseases, especially hyperplastic and neoplastic diseases.

The most common methods of selective treatment are currently surgery, chemotherapy and external beam irradiation. Targeted radionuclide therapy is, however, a promising and developing area with the potential to deliver highly cytotoxic radiation to unwanted cell types. The most common forms of radiopharmaceutical currently authorised for use in humans employ beta-emitting and/or gamma-emitting radionuclides. There has, however, been some interest in the use of alpha-emitting radionuclides in therapy because of their potential for more specific cell killing.

The radiation range of typical alpha emitters in physiological surroundings is generally less than 100 micrometers, the equivalent of only a few cell diameters. This makes these sources well suited for the treatment of tumours, including micrometastases, because if they are well targeted then little of the radiated energy will pass beyond the target cells. Thus, damage to surrounding healthy tissue may be minimised (see Feinendegen et al., Radiat Res 148:195-201 (1997)). In contrast, a beta particle has a range of 1 mm or more in water (see Wilbur, Antibody Immunocon Radiopharm 4: 85-96 (1991)).

The energy of alpha-particle radiation is high in comparison with that carried by beta particles, gamma rays and X-rays, typically being 5-8 MeV, or 5 to 10 times that of a beta particle and 20 or more times the energy of a gamma ray. Thus, this deposition of a large amount of energy over a very short distance gives α-radiation an exceptionally high linear energy transfer (LET), high relative biological efficacy (RBE) and low oxygen enhancement ratio (OER) compared to gamma and beta radiation (see Hall, "Radiobiology for the radiologist", Fifth edition, Lippincott Williams & Wilkins, Philadelphia Pa., USA, 2000). This explains the exceptional cytotoxicity of alpha emitting radionuclides and also imposes stringent demands on the biological targeting of such isotopes and upon the level of control and study of alpha emitting radionuclide distribution which is necessary in order to avoid unacceptable side effects.

Table 1 below shows the physical decay properties of the alpha emitters so far broadly proposed in the literature as possibly having therapeutic efficacy.

TABLE 1

| Candidate nuclide | $T_{1/2}$* | Clinically tested for |
|---|---|---|
| $^{225}$Ac | 10.0 days | leukaemia |
| $^{211}$At | 7.2 hours | glioblastoma |
| $^{213}$Bi | 46 minutes | leukaemia |
| $^{223}$Ra | 11.4 days | skeletal metastases |
| $^{224}$Ra | 3.66 days | ankylosing spondylitis |

*Half life

So far, with regards to the application in radioimmunotherapy the main attention has been focused on $^{211}$At, $^{213}$Bi and $^{225}$Ac and these three nuclides have been explored in clinical immunotherapy trials.

Several of the radionuclides which have been proposed are short-lived, i.e. have half lives of less than 12 hours. Such short half-lives makes it difficult to produce and distribute radiopharmaceuticals based upon these radionuclides in a commercial manner. Administration of a short-lived nuclide also increases the proportion of the radiation dose which will be emitted in the body before the target site is reached.

The recoil energy from alpha-emission will in many cases cause the release of daughter nuclides from the position of decay of the parent. This recoil energy is sufficient to break many daughter nuclei out from the chemical environment which may have held the parent, e.g. where the parent was complexed by a ligand such as a chelating agent. This will occur even where the daughter is chemically compatible with, i.e. complexable by, the same ligand. Equally, where the daughter nuclide is a gas, particularly a noble gas such as radon, or is chemically incompatible with the ligand, this release effect will be even greater. When daughter nuclides have half-lives of more than a few seconds, they can diffuse away into the blood system, unrestrained by the complexant which held the parent. These free radioactive daughters can then cause undesired systemic toxicity.

The use of Thorium-227 ($T_{1/2}$=18.7 days) under conditions where control of the $^{223}$Ra daughter isotope was proposed a few years ago (see WO 01/60417 and WO 02/05859). This was in situations where a carrier system is used which allows the daughter nuclides to be retained by a closed environment. In one case, the radionuclide is disposed within a liposome and the substantial size of the liposome (as compared to recoil distance) helps retain daughter nuclides within the liposome. In the second case, bone-seeking complexes of the radionuclide are used which incorporate into the bone matrix and therefore restrict release of the daughter nuclides. These are potentially highly advantageous methods, but the administration of liposomes is not desirable in some circumstances and there are many diseases of soft tissue in which the radionuclides cannot be surrounded by a mineralized matrix so as to retain the daughter isotopes.

More recently, it was established that the toxicity of the $^{223}$Ra daughter nuclei released upon decay of $^{227}$Th could be tolerated in the mammalian body to a much greater extent than would be predicted from prior tests on comparable nuclei. In the absence of the specific means of retaining the radium daughters of thorium-227 discussed above, the publicly available information regarding radium toxicity made it clear that it was not possible to use thorium-227 as a therapeutic agent since the dosages required to achieve a therapeutic effect from thorium-227 decay would result in a highly toxic and possibly lethal dosage of radiation from the decay of the radium daughters, i.e. there is no therapeutic window.

WO 04/091668 describes the unexpected finding that a therapeutic treatment window does exist in which a therapeutically effective amount of a targeted thorium-227 radionuclide can be administered to a subject (typically a mammal) without generating an amount of radium-223 sufficient to cause unacceptable myelotoxicity. This can therefore be used for treatment and prophylaxis of all types of diseases at both bony and soft-tissue sites.

In view of the above developments, it is now possible to employ alpha-emitting thorium-227 nuclei in endoradionuclide therapy without lethal myelotoxicity resulting from the generated $^{223}$Ra. Nonetheless, the therapeutic window remains relatively narrow and it is in all cases desirable to administer no more alpha-emitting radioisotope to a subject than absolutely necessary. Useful exploitation of this new therapeutic window would therefore be greatly enhanced if the alpha-emitting thorium-227 nuclei could be complexed and targeted with a high degree of reliability.

Because radionuclides are constantly decaying, the time spent handling the material between isolation and administration to the subject is of great importance. It would also be of considerable value if the alpha-emitting thorium nuclei could be complexed, targeted and/or administered in a form which was quick and convenient to prepare, preferably requiring few steps, short incubation periods and/or temperatures not irreversibly affecting the properties of the targeting entity.

The present inventors have now unexpectedly established that the use of a 4+ thorium-227 ion complexed by an octadentate hydroxypyridinone (HOPO)-type ligand linked to a targeting moiety provides a remarkable degree of control over the thorium-227 ion. Furthermore, such complexes may be relatively quickly and/or easily prepared using the methods described herein.

SUMMARY OF THE INVENTION

Viewed from one aspect the present invention therefore provides a tissue-targeting complex comprising a tissue targeting moiety, an octadentate hydroxypyridinone-containing ligand and the ion of an alpha-emitting thorium radionuclide. A particularly preferable aspect is such a tissue-targeting complex comprising a polypeptide tissue-targeting moiety covalently bound to an octadentate ligand comprising at least one 3,2-hydroxypyridinone moiety, said ligand complexed to the 4+ ion of and alpha-emitting thorium radionuclide such as $^{227}$Th.

Viewed from a further aspect the invention provides the use of a tissue-targeting complex comprising a tissue targeting moiety, an octadentate hydroxypyridinone-containing ligand and the ion of an alpha-emitting thorium radionuclide (including any such complex described herein) in the manufacture of a medicament for the treatment of hyperplastic or neoplastic disease including any such disease described herein.

In a corresponding aspect, the invention provides a method of treatment of a human or non-human animal (particularly one in need thereof) comprising administration of at least one tissue-targeting complex comprising a tissue targeting moiety, an octadentate hydroxypyridinone-containing ligand and the ion of an alpha-emitting thorium radionuclide (including any such complex described herein). Such a method is preferably for the treatment of hyperplastic or neoplastic disease including any such disease described herein.

Viewed from a further aspect the invention provides a pharmaceutical composition comprising a tissue-targeting complex comprising a tissue targeting moiety, an octadentate hydroxypyridineone-containing ligand and the ion of an alpha-emitting thorium radionuclide (including any such complex described herein) together with at least one pharmaceutical carrier or excipient.

So as to distinguish from thorium complexes of the most abundant naturally occurring thorium isotope, i.e. thorium-232 (half-life $10^{10}$ years and effectively non-radioactive), it should be understood that the thorium complexes and the compositions thereof claimed herein include the alpha-emitting thorium radioisotope (i.e. at least one isotope of thorium with a half-life of less than $10^3$ years, e.g. thorioum-227) at greater than natural relative abundance, eg at least 20% greater. This need not affect the definition of the method of the invention where a therapeutically effective amount of a radioactive thorium, such as thorium-227 is explicitly required, but will preferably be the case in all aspects.

Viewed from a yet still further aspect the invention also provides a kit for use in a method according to the invention, said kit comprising a tissue targeting moiety, conjugated or conjugatable to an octadentate hydroxypyridineone-containing ligand. All binding moieties and ligands preferably being those described herein. Such a kit will optionally and preferably include an alpha-emitting thorium radionuclide, such as $^{227}$Th.

DETAILED DESCRIPTION OF THE INVENTION

In the context of the present invention, "tissue targeting" is used herein to indicate that the substance in question (particularly when in the form of a conjugate to a thorium complex), serves to localise itself (and particularly to localise any conjugated thorium complex) preferentially to at least one tissue site at which its presence (e.g. to deliver a radioactive decay) is desired. The targeting moiety may, for example, bind to cell-surface markers (e.g. receptors, transport proteins, cell adhesion molecules etc) present on disease-affected cells or on cells in the vicinity of disease affected cells. Such call-surface markers include proteins more heavily expressed on diseased cell surfaces than on healthy cell surfaces or those more heavily expressed on cell surfaces during periods of growth or replication than during dormant phases. Components present in the vicinity of target cells or tissues or associated therewith may also be utilised at the target for therapy in accordance with any aspect of the invention. For example, components present in or released into the matrix around targeted cells or tissues may be used for targeting if the presence, form or concentration allows the region to be distinguished from healthy tissue. Examples of this are matrix antigens such as tenascin, which is associated with brain tumours but is expressed in the matrix between cells. Such matrix antigens can be targeted by a single or composite targeting moiety as discussed herein.

The tissue targeting moiety may also comprise two or more components collectively having the effect of targeting the thorium complex to the desired tissue(s). This may be, for example, where one component is administered first and binds to a particular tissue, tumour or cell-type (a tissue-binding agent) and a second and/or further component (linking agent) is administered simultaneously, or preferably subsequently, which binds in vivo to the tissue-binding agent. The linking agent would be conjugated directly or indirectly to the complexed alpha-emitting thorium and thus collectively the tissue-binding and linking agents would form a tissue-targeting moiety. Suitable specific binding pairs suitable for providing the tissue binding agent and linking agent with mutual affinity are well known in the art (e.g. biotin with avidin or streptavidin).

The various aspects of the invention as described herein relate to treatment of disease, particularly for the selective targeting of diseased tissue, as well as relating to complexes, conjugates, medicaments, formulation, kits etc useful in such methods. In all aspects, the diseased tissue may reside at a single site in the body (for example in the case of a localised solid tumour) or may reside at a plurality of sites (for example where several joints are affected in arthritis or in the case of a distributed or metastasized cancerous disease).

The diseased tissue to be targeted may be at a soft tissue site, at a calcified tissue site or a plurality of sites which may all be in soft tissue, all in calcified tissue or may include at least one soft tissue site and/or at least one calcified tissue site. In one embodiment, at least one soft tissue site is targeted. The sites of targeting and the sites of origin of the disease may be the same, but alternatively may be different. Where more than one site is involved this may include the site of origin or may be a plurality of secondary sites.

The term "soft tissue" is used herein to indicate tissues which do not have a "hard" mineralized matrix. In particular, soft tissues as used herein may be any tissues that are not skeletal tissues. Correspondingly, "soft tissue disease" as used herein indicates a disease occurring in a "soft tissue" as used herein. The invention is particularly suitable for the treatment of cancers and "soft tissue disease" thus encompasses carcinomas, sarcomas, myelomas, leukemias, lymphomas and mixed type cancers occurring in any "soft" (i.e. non-mineralized) tissue, as well as other non-cancerous diseases of such tissue. Cancerous "soft tissue disease" includes solid tumours occurring in soft tissues as well as metastatic and micro-metastatic tumours. Indeed, the soft tissue disease may comprise a primary solid tumour of soft tissue and at least one metastatic tumour of soft tissue in the same patient. Alternatively, the "soft tissue disease" may consist of only a solid tumour or only metastases with the primary tumour being a skeletal disease.

It is a key recent finding that certain alpha-radioactive thorium isotopes (e.g. 227Th) may be administered in an amount that is both therapeutically effective and does not generate intolerable myelotoxicity. As used herein, the term "acceptably non-myelotoxic" is used to indicate that, most importantly, the amount of radium-223 generated by decay of the administered thorium-227 radioisotope is generally not sufficient to be directly lethal to the subject. It will be clear to the skilled worker, however, that the amount of marrow damage (and the probability of a lethal reaction) which will be an acceptable side-effect of such treatment will vary significantly with the type of disease being treated, the goals of the treatment regimen, and the prognosis for the subject. Although the preferred subjects for the present invention are humans, other mammals, particularly dogs, will benefit from the use of the invention and the level of acceptable marrow damage may also reflect the species of the subject. The level of marrow damage acceptable will generally be greater in the treatment of malignant disease than for non-malignant disease. One well known measure of the level of myelotoxicity is the neutrophil cell count and, in the present invention, an acceptably non-myelotoxic amount of $^{223}$Ra will typically be an amount controlled such that the neutrophil count at its lowest point (nadir) is no less than 10% of the count prior to treatment. Preferably, the acceptably non-myelotoxic amount of $^{223}$Ra will be an amount such that the neutrophil cell fraction is at least 20% at nadir and more preferably at least 30%. A nadir neutrophil cell fraction of at least 40% is most preferred.

In addition, radioactive thorium (e.g. $^{227}$Th) containing compounds may be used in high dose regimens where the myelotoxicity of the generated radium (e.g. $^{223}$Ra) would normally be intolerable when stem cell support or a comparable recovery method is included. In such cases, the neutrophil cell count may be reduced to below 10% at nadir and exceptionally will be reduced to 5% or if necessary below 5%, providing suitable precautions are taken and subsequent stem cell support is given. Such techniques are well known in the art.

A thorium isotope of particular interest in the present invention is thorium-227, and thorium-227 is the preferred isotope for all references to thorium herein where context allows. Thorium-227 is relatively easy to produce and can be prepared indirectly from neutron irradiated $^{226}$Ra, which will contain the mother nuclide of $^{227}$Th, i.e. $^{227}$Ac ($T_{1/2}$=22 years). Actinium-227 can quite easily be separated from the $^{226}$Ra target and used as a generator for $^{221}$Th. This process can be scaled to industrial scale if necessary, and hence the supply problem seen with most other alpha-emitters considered candidates for molecular targeted radiotherapy can be avoided.

Thorium-227 decays via radium-223. In this case the primary daughter has a half-life of 11.4 days. From a pure $^{227}$Th source, only moderate amounts of radium are produced during the first few days. However, the potential toxicity of $^{223}$Ra is higher than that of $^{227}$Th since the emission from $^{223}$Ra of an alpha particle is followed within minutes by three further alpha particles from the short-lived daughters (see Table 2 below which sets out the decay series for thorium-227).

TABLE 2

| Nuclide | Decay mode | Mean particle energy (MeV) | Half-life |
|---|---|---|---|
| $^{227}$Th | α | 6.02 | 18.72 days |
| $^{223}$Ra | α | 5.78 | 11.43 days |
| $^{219}$Rn | α | 6.88 | 3.96 seconds |
| $^{215}$Po | α | 7.53 | 1.78 ms |
| $^{211}$Pb | β | 0.45 | 36.1 minutes |
| $^{211}$Bi | α | 6.67 | 2.17 minutes |
| $^{207}$Tl | β | 1.42 | 4.77 minutes |
| $^{207}$Pb | | | Stable |

Partly because it generates potentially harmful decay products, thorium-227 ($T_{1/2}$=18.7 days) has not been widely considered for alpha particle therapy.

Thorium-227 may be administered in amounts sufficient to provide desirable therapeutic effects without generating so much radium-223 as to cause intolerable bone marrow suppression. It is desirable to maintain the daughter isotopes in the targeted region so that further therapeutic effects may be derived from their decay. However, it is not necessary to maintain control of the thorium decay products in order to have a useful therapeutic effect without inducing unacceptable myelotoxicity.

Assuming the tumour cell killing effect will be mainly from thorium-227 and not from its daughters, the likely therapeutic dose of this isotope can be established by comparison with other alpha emitters. For example, for astatine-211, therapeutic doses in animals have been typically 2-10 MBq per kg. By correcting for half-life and energy the corresponding dosage for thorium-227 would be at least 36-200 kBq per kg of bodyweight. This would set a lower limit on the amount of $^{227}$Th that could usefully be administered in expectation of a therapeutic effect. This calculation assumes comparable retention of astatine and thorium. Clearly however the 18.7 day half-life of the thorium will most likely result in greater elimination of this isotope before its decay. This calculated dosage should therefore normally be considered to be the minimum effective amount. The therapeutic dose expressed in terms of fully retained $^{227}$Th (i.e. $^{227}$Th which is not eliminated from the body) will typically be at least 18 or 25 kBq/kg, preferably at least 36 kBq/kg and more preferably at least 75 kBq/kg, for example 100 kBq/kg or more. Greater amounts of thorium would be expected to have greater therapeutic effect but cannot be administered if intolerable side effects will result. Equally, if the thorium is administered in a form having a short biological half-life (i.e. the half life before elimination from the body still carrying the thorium), then greater amounts of the radioisotope will be required for a therapeutic effect because much of the thorium will be eliminated before it decays. There will, however, be a corresponding decrease in the amount of radium-223 generated. The above amounts of thorium-227 to be administered when the isotope is fully retained may easily be related to equivalent doses with shorter biological half-lives. Such calculations are well known in the art and given in WO 04/091668 (e.g. in the text an in Examples 1 and 2).

If a radiolabelled compound releases daughter nuclides, it is important to know the fate, if applicable, of any radioactive daughter nuclide(s). With $^{227}$Th, the main daughter product is $^{223}$Ra, which is under clinical evaluation because of its bone seeking properties. Radium-223 clears blood very rapidly and is either concentrated in the skeleton or excreted via intestinal and renal routes (see Larsen, J Nucl Med 43(5, Supplement): 160P (2002)). Radium-223 released in vivo from $^{227}$Th may therefore not affect healthy soft tissue to a great extent. In the study by Müller in Int. J. Radiat. Biol. 20:233-243 (1971) on the distribution of $^{227}$Th as the dissolved citrate salt, it was found that $^{223}$Ra generated from $^{227}$Th in soft tissues was readily redistributed to bone or was excreted. The known toxicity of alpha emitting radium, particularly to the bone marrow, is thus an issue with thorium dosages.

It was established for the first time in WO 04/091668 that, in fact, a dose of at least 200 kBq/kg of $^{223}$Ra can be administered and tolerated in human subjects. These data are presented in that publication. Therefore, it can now be seen that, quite unexpectedly, a therapeutic window does exist in which a therapeutically effective amount of $^{227}$Th (such as greater than 36 kBq/kg) can be administered to a mammalian subject without the expectation that such a subject will suffer an unacceptable risk of serious or even lethal myelotoxicity. Nonetheless, it is extremely important that the best use of this therapeutic window be made and therefore it is essential that the radioactive thorium be quickly and efficiently complexed, and held with very high affinity so that the greatest possible proportion of the dose is delivered to the target site.

The amount of $^{223}$Ra generated from a $^{227}$Th pharmaceutical will depend on the biological half-life of the radiolabeled compound. The ideal situation would be to use a complex with a rapid tumor uptake, including internalization into tumor cell, strong tumor retention and a short biological half-life in normal tissues. Complexes with less than ideal biological half-life can however be useful as long as the dose of $^{223}$Ra is maintained within the tolerable level. The amount of radium-223 generated in vivo will be a factor of the amount of thorium administered and the biological retention time of the thorium complex. The amount of radium-223 generated in any particular case can be easily calculated by one of ordinary skill. The maximum administrable amount of $^{227}$Th will be determined by the amount of radium generated in vivo and must be less than the amount that will produce an intolerable level of side effects, particularly myelotoxicity. This amount will generally be less than 300 kBq/kg, particularly less than 200 kBq/kg and more preferably less than 170 kBq/kg (e.g less than 130 kBq/kg). The minimum effective dose will be determined by the cytotoxicity of the thorium, the susceptibility of the diseased tissue to generated alpha irradiation and the degree to which the thorium is efficiently combined, held and delivered by the targeting complex (being the combination of the ligand and the targeting moiety in this case).

In the method of invention, the thorium complex is desirably administered at a thorium-227 dosage of 18 to 400 kBq/kg bodyweight, preferably 36 to 200 kBq/kg, (such as 50 to 200 kBq/kg) more preferably 75 to 170 kBq/kg, especially 100 to 130 kBq/kg. Correspondingly, a single dosage until may comprise around any of these ranges multiplied by a suitable bodyweight, such as 30 to 150 Kg, preferably 40 to 100 Kg (e.g. a range of 540 kBq to 4000 KBq per dose etc). The thorium dosage, the complexing agent and the administration route will moreover desirably be such that the radium-223 dosage generated in vivo is less than 300 kBq/kg, more preferably less than 200 kBq/kg, still more preferably less than 150 kBq/kg, especially less than 100 kBq/kg. Again, this will provide an exposure to $^{223}$Ra indicated by multiplying these ranges by any of the bodyweights indicated. The above dose levels are preferably the fully retained dose of $^{227}$Th but may be the administered dose taking into account that some $^{227}$Th will be cleared from the body before it decays.

Where the biological half-life of the $^{227}$Th complex is short compared to the physical half-life (e.g. less than 7 days, especially less than 3 days) significantly larger administered doses may be needed to provide the equivalent retained dose. Thus, for example, a fully retained dose of 150 kBq/kg is equivalent to a complex with a 5 day half-life administered at a dose of 711 kBq/kg. The equivalent administered dose for any appropriate retained doses may be calculated from the biological clearance rate of the complex using methods well known in the art.

Since the decay of one $^{227}$Th nucleus provides one $^{223}$Ra atom, the retention and therapeutic activity of the $^{227}$Th will be directly related to the $^{223}$Ra dose suffered by the patient. The amount of $^{223}$Ra generated in any particular situation can be calculated using well known methods.

In a preferred embodiment, the present invention therefore provides a method for the treatment of disease in a mammalian subject (as described herein), said method comprising administering to said subject a therapeutically effective quantity of a conjugate comprising a tissue targeting moiety, an octadentate ligand (especially any of those described herein) and a radioactive thorium isotope (e.g. thorium-227).

It is obviously desirable to minimise the exposure of a subject to the $^{223}$Ra daughter isotope, unless the properties of this are usefully employed. In particular, the amount of radium-223 generated in vivo will typically be greater than 40 kBq/kg, e.g. greater than 60 kBq/Kg. In some cases it will be necessary for the $^{223}$Ra generated in vivo to be more than 80 kBq/kg, e.g. greater than 100 or 115 kBq/kg.

Thorium-227 labelled conjugates in appropriate carrier solutions may be administered intravenously, intracavitary (e.g. intraperitoneally), subcutaneously, orally or topically, as a single application or in a fractionated application regimen. Preferably the complexes conjugated to a targeting moiety will be administered as solutions by a parenteral (e.g. transcutaneous) route, especially intravenously or by an intracavitary route. Preferably, the compositions of the present invention will be formulated in sterile solution for parenteral administration.

Thorium-227 in the methods and products of the present invention can be used alone or in combination with other treatment modalities including surgery, external beam radiation therapy, chemotherapy, other radionuclides, or tissue temperature adjustment etc. This forms a further, preferred embodiment of the method of the invention and formulations/medicaments may correspondingly comprise at least one additional therapeutically active agent such as another radioactive agent or a chemotherapeutic agent.

In one particularly preferred embodiment the subject is also subjected to stem cell treatment and/or other supportive therapy to reduce the effects of radium-223 induced myelotoxicity.

According to this invention $^{227}$Th may be complexed by targeting complexing agents. Typically the targeting moieties will have a molecular weight from 100 g/mol to several million g/mol (particularly 100 g/mol to 1 million g/mol), and will preferably have affinity for a disease-related receptor either directly, and/or will comprise a suitable pre-administered binder (e.g. biotin or avidin) bound to a molecule that has been targeted to the disease in advance of administering $^{227}$Th. Suitable targeting moieties include poly- and oligo-peptides, proteins, DNA and RNA fragments, aptamers etc, preferably a protein, e.g. avidin, streptavidin, a polyclonal or monoclonal antibody (including IgG and IgM type antibodies), or a mixture of proteins or fragments or constructs of protein. Antibodies, antibody constructs, fragments of antibodies (e.g. FAB fragments or any fragment comprising at least one antigen binding region(s)), constructs of fragments (e.g. single chain antibodies) or a mixture thereof are particularly preferred.

Also suitable for use in the present invention are therapeutic conjugates of complexed $^{227}$Th with a peptide, amino acid, steroidal or non-steroidal hormone, folate, estrogen, testosterone, biotin, or other specific-binding compounds with molecular weight typically below 10 000 g/mol.

Generally, the octadentate ligand is conjugated directly or indirectly (e.g. via a linker moiety) to the targeting moiety. General constructs of this type; i.e. of active (e.g. therapeutically or diagnostically active) metal-complexing moiety-optional linker moiety-targeting moiety, are well known in the fields of targeted radiopharmaceuticals and targeted imaging agents. However, little or no work is available assessing the suitability of various ligands for specific use with thorium 4+ ions. In this regard reference may be had for example to "Handbook of Targeted Delivery of Imaging Agents", Ed. Torchilin, CRC Press, 1995.

Previously known chelators for thorium include the polyaminopolyacid chelators which comprise a linear, cyclic or branched polyazaalkane backbone with acidic (e.g. carboxyalkyl) groups attached at backbone nitrogens. Examples of such chelators include DOTA derivatives such as p-isothiocyanatobenzyl-1,4,7,10-tetraazacyclododecane-1,4,7,10-tetraacetic acid (p-SCN-Bz-DOTA) and DTPA derivatives such as p-isothiocyanatobenzyl-diethylenetriaminepentaacetic acid (p-SCN-Bz-DTPA), the first being cyclic chelators, the latter linear chelators.

Derivatives of 1,4,7,10-tetraazacyclododecane-1,4,7,10-tetraacetic acid have been previously exemplified, but standard methods cannot easily be used to chelate thorium with DOTA derivatives. Heating of the DOTA derivative with the metal provides the chelate effectively, but often in low yields. There is a tendency for at least a portion of the ligand to irreversibly denature during the procedure. Furthermore, because of its relatively high susceptibility to irreversible denaturation, it is generally necessary to avoid attachment of the targeting moiety until all heating steps are completed. This adds an extra chemical step (with all necessary work-up and separation) which must be carried out during the decay lifetime of the alpha-emitting thorium isotope. Obviously it is preferable not to handle alpha-emitting material in this way or to generate corresponding waste to a greater extent than necessary. Furthermore, all time spend preparing the conjugate wastes a proportion of the thorium which will decay during this preparatory period.

It is preferred that the complexes of alpha-emitting thorium and an octadentate ligand in all aspects of the present invention are formed or formable without heating above 60° C. (e.g. without heating above 50° C.), preferably without heating above 38° C. and most preferably without heating above 25° C.

It is additionally preferred that the conjugate of the targeting moiety and the octadentate ligand be prepared prior to addition of the alpha-emitting thorium isotope (e.g. $^{227}$Th$^{4+}$ ion). The products of the invention are thus preferably formed or formable by complexation of alpha-emitting thorium isotope (e.g. $^{227}$Th$^{4+}$ ion) by a conjugate of an octadentate ligand and a tissue-targeting moiety.

The chelators may be non-phosphonate molecules and in one embodiment of the present invention the $^{227}$Th will not be attached to any phosphonate or other bone-targeting group nor administered with such materials.

Types of targeting compounds that may be linked to thorium (e.g. thorium-227) via an octadentate chelator (comprising a coupling moiety as described herein). The targeting moiety may be selected from known targeting groups, which include monoclonal or polyclonal antibodies, growth factors, peptides, hormones and hormone analogues, folate and folate derivatives, botin, avidin and streptavidin or analogues thereof. Other possible carriers could be RNA, DNA, or fragments thereof, oligonucleotides, carbohydrates, lipids or compounds made by combining such groups with or without proteins etc.

The tissue targeting moiety may, in one embodiment, exclude bone-seekers, liposomes and folate conjugated antibodies or antibody fragments. Alternatively, such moieties may be included.

The thorium (e.g. thorium-227) labelled molecules of the invention may be used for the treatment of cancerous or non-cancerous diseases by targeting disease-related receptors. Typically, such a medical use of $^{227}$Th will be by radioimmunotherapy based on linking $^{227}$Th by a chelator to an antibody, an antibody fragment, or a construct of antibody or antibody fragments for the treatment of cancerous or non-cancerous diseases. The use of $^{227}$Th in methods and pharmaceuticals according to the present invention is particularly suitable for the treatment of any form of cancer including carcinomas, sarcomas, lymphomas and leukemias, especially cancer of the lung, breast, prostate, bladder, kidney, stomach, pancreas, oesophagus, brain, ovary, uterus, oral cancer, colorectal cancer, melanoma, multiple myeloma and non-Hodgkin's lymphoma.

The amount of $^{223}$Ra released could be diminished if the molecule carrying $^{227}$Th has a short biological retention half-time in vivo because the radionuclide will mostly be eliminated before a high proportion of the $^{227}$Th has decayed to $^{223}$Ra. The amount of $^{227}$Th would, however, need to be increased in order to remain therapeutically effective, according to the present invention. If the complexing agent is selected so as to deliver the $^{227}$Th into the interior of the targeted cells, this will further increase the specific cytotoxicity and reduce the systemic toxic effect of the radioactive daughters because of at least partial retention of daughter isotopes at the tumour site. Both of these features widen the $^{227}$Th therapeutic window and thus form preferred embodiments of the invention.

In a further embodiment of the invention, patients with both soft tissue and skeletal disease may be treated both by the $^{227}$Th and by the $^{223}$Ra generated in vivo by the administered thorium. In this particularly advantageous aspect, an extra therapeutic component to the treatment is derived from the acceptably non-myelotoxic amount of $^{223}$Ra by the targeting of the skeletal disease. In this therapeutic method, $^{227}$Th is typically utilised to treat primary and/or metastatic cancer of soft tissue by suitable targeting thereto and the $^{223}$Ra generated from the $^{227}$Th decay is utilised to treat related skeletal disease in the same subject. This skeletal disease may be metastases to the skeleton resulting from a primary soft-tissue cancer, or may be the primary disease where the soft-tissue treatment is to counter a metastatic cancer. Occasionally the soft tissue and skeletal diseases may be unrelated (e.g. the additional treatment of a skeletal disease in a patient with a rheumatological soft-tissue disease).

A key aspect of the present invention in all respects is the use of an octadentate ligand, particularly an octadentate hydroxypyridinone-containing ligand. Such ligands will typically comprise at least one chelating group of the following substituted pyridine structure (I):

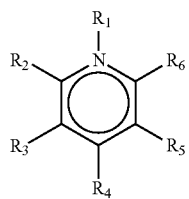

I

Wherein $R_1$ is an optional N-substituent group and may thus be absent or may be selected from hydrocarbyl, OH, O-hydrocarbyl, SH and S-hydrocarby groups, where any or each hydrocarbyl moiety is independently selected from short hydrocarbyl groups, such as C1 to C8 hydrocarbyl, including C1 to C8 alkyl, alkenyl or alkynyl groups, or may be an OH or O-hydrocarbyl. $R_1$ may also comprise a linker moiety, as indicated below and/or may comprise a coupling moiety as also indicated below.

In Formula I, groups $R_2$ to $R_6$ may each independently be selected from H, OH, =O, short hydrocarbyl (as described herein), a linker moiety (as described herein) and/or a coupling moiety (as described herein). At least one of groups $R_1$ to $R_6$ will be OH. Generally, at least one of groups $R_2$ to $R_6$ will be =O. Generally, at least one of groups $R_1$ to $R_6$ will be a linker moiety (as described herein).

Preferably, exactly one of groups $R_2$ to $R_6$ will be =O. Preferably exactly one of groups $R_1$ to $R_6$ will be OH. Preferably exactly one of groups $R_1$ to $R_6$ will be a linker moiety (as described herein). The remaining groups $R_1$ to $R_6$ may be any of those moieties indicated herein, but are preferably H. Where a linker moiety or any additional linker, template or chelating groups attached to a linker moiety do not comprise a coupling moiety then one of groups $R_1$ to $R_6$ is preferably a coupling moiety (as described herein).

In a preferred embodiment, one of groups $R_1$ to $R_6$ will be OH and one of $R_2$ to $R_6$ will be =O and the OH and =O groups will be on neighbouring atoms of the ring. Thus, in a preferred embodiment, OH and =O may be on atoms 1,2; 2,3; 3,2; 3,4; or 4,3 respectively (numbering from the nitrogen as would be expected). Octadentate ligands having at least one chelating moiety wherein OH and =O groups are present at positions 3 and 2 respectively are highly preferred. The octadentate ligands may have 2, 3 or 4 such chelating groups, where 2 or 4 such groups are highly preferred.

Suitable chelating moieties may be formed by methods known in the art, including the methods described in U.S. Pat. No. 5,624,901 (e.g. examples 1 and 2) and WO2008/063721 (both incorporated herein by reference).

As used herein, the term "linker moiety" ($R_L$ in formula II) is used to indicate a chemical entity which serves to join at least two chelating groups in the octadentate ligands, which form a key component in various aspects of the invention. Typically, each chelating group (e.g. those of formula I above and/or formula II below) will be bi-dentate and so four chelating groups, of which at least one is of formula I, will typically be present in the ligand. Such chelating groups are joined to each other by means of their linker moieties. Thus, a linker moiety (e.g. group $R_L$ below) may be shared between more than one chelating group of formula I and/or II. The linker moieties may also serve as the point of attachment between the complexing part of the octadentate ligand and the targeting moiety. In such a case, at least one linker moiety will join to a coupling moiety ($R_C$). Suitable linker moieties include short hydrocarbyl groups, such as C1 to C12 hydrocarbyl, including C1 to C12 alkyl, alkenyl or alkynyl group, including methyl, ethyl, propyl, butyl, pentyl and/or hexyl groups of all topologies.

Linker moieties may also be or comprise any other suitably robust chemical linkages including esters, ethers, amine and/or amide groups. The total number of atoms joining two chelating moieties (counting by the shortest path if more than one path exists) will generally be limited, so as to constrain the chelating moieties in a suitable arrangement for complex formation. Thus, linker moieties will typically be chosen to provide no more than 15 atoms between chelating moieties, preferably, 1 to 12 atoms, and more preferably 1 to 10 atoms between chelating moieties. Where a linker moiety joins two chelating moieties directly, the linker will typically be 1 to 12 atoms in length, preferably 2 to 10 (such as ethyl, propyl, n-butyl etc). Where the linker moiety joins to a central template (see below) then each linker may be shorter with two separate linkers joining the chelating moieties. A linker length of 1 to 8 atoms, preferably 1 to 6 atoms may be preferred in this case (methyl, ethyl and propyl being suitable, as are groups such as these having an ester, ether or amide linkage at one end or both).

In addition to the linker moiety, which primarily serves to link the various chelating groups of the octadentate ligand to each other and/or to a central template, the octadentate preferably further comprises a "coupling moiety" ($R_C$). The function of the coupling moiety is to link the octadentate ligand to the targeting moiety. This may be achieved by either covalent or non-covalent attachment (e.g. by a specific binding pair such as biotin/avidin (streptavidin). Preferably coupling moieties will be covalently linked to the chelating groups, either by direct covalent attachment to one of the chelating groups or more typically by attachment to a linker moiety or template. Should two or more coupling moieties be used, each can be attached to any of the available sites such as on any template, linker or chelating group.

In one embodiment, the coupling moiety may have the structure:

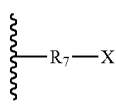

wherein $R_7$ is a bridging moiety, which is a member selected from substituted or unsubstituted alkyl, substituted or unsubstituted heteroalkyl, substituted or unsubstituted heterocycloalkyl, substituted or unsubstituted aryl and substituted or unsubstituted heteroaryl; and X is a targeting moiety or a reactive functional group. The preferred bridging moieties include all those groups indicated herein as suitable linker moieties. Preferred targeting moieties include all of those described herein and preferred reactive X groups include any group capable of forming a covalent linkage to a targeting moiety, including, for example, COOH, OH, SH, NHR and COH groups, where the R of NHR may be H or any of the short hydrocarbyl groups described herein. Highly preferred groups for attachment onto the targeting moiety include epsilon-amines of lysine residues and thiol groups of cysteine residues. Non-limiting examples of suitable reactive X groups, include N-hydroxysuccimidylesters, imidoesters, acylhalides, N-maleimides, alpha-halo acetyl and isothiocyanates, where the latter three are suitable for reaction with a thiol group.

The coupling moiety is preferably attached, so that the resulting coupled octadentate ligand will be able to undergo formation of stable metal ion complexes. The coupling moiety will thus preferably link to the linker, template or chelating moiety at a site which does not significantly interfere with the complexation. Such a site will preferably be on the linker or template, more preferably at a position distant from the surface binding to the target.

Preferred chelating groups include those of formula II below:

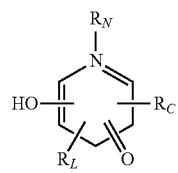

II

In the above formula II, the =O moiety represents a keto-group attached to any carbon of the pyridine ring, the —OH represents a hydroxy moiety attached to any atom of the pyridine ring and the —$R_L$ represents a linker moiety which attaches the hydroxypyridinone moiety to other complexing moieties so as to form the overall octadentate ligand. Any linker moiety described herein is suitable as $R_L$ including short hydrocarbyl groups, such as C1 to C8 hydrocarbyl, including C1 to C8 alkyl, alkenyl or alkynl group, including methyl, ethyl, propyl, butyl, pentyl and/or hexyl groups of all topologies. $R_L$ may join the ring of formula II at any atom of the pyridine ring, such as a carbon or nitrogen atom. The $R_L$ groups may then in turn bond directly to another chelating moiety, to another linker group and/or to a central atom or group, such as a ring or other template (as described herein). The linkers, chelating groups and optional template moieties are selected so as to form an appropriate octadentate ligand.

In one preferred embodiment the —OH and =O moieties of formula II reside on neighbouring atoms of the pyridine ring, such that 1,2-; 2,3-, 3,2-; 4,3-; and 3,4-hydroxypyridinone derivatives are all highly suitable.

Where the OH group or the linker moiety $R_L$ reside on the nitrogen of the pyridine ring, group $R_N$ will generally be absent. However, where present, $R_N$ may be any suitable moiety including substituted or unsubstituted hydrocarbyl groups, particularly the short hydrocarbyl groups indicated herein.

In one preferred embodiment, at least one 3,2-hydroxypyridinone moiety is present in the octadentate ligand structure. This may evidently be substituted by any of the various substituent moieties indicated herein.

Since each of the moieties of formula II has two potentially complexing oxygens, one embodiment of the present invention provides for an octadentate ligand comprising at least 2, preferably at least 3 and most preferably 4 independently chosen moieties of formula I. Each moiety of formula II may have an independent substitution pattern, but in one preferred embodiment, at least one moiety is a 3,2-hydroxypyridinone moiety. The ligand may include 2, 3 or 4 3,2-hydroxypyridinone moieties (substituted as appropriate, as described herein).

Each moiety of formula I or II in the octadentate ligand may be joined to the remainder of the ligand by any appropriate linker group as discussed herein and in any appropriate topology. For example, four groups of formula I may be joined by their linker groups to a backbone so as to form a linear ligand, or may be bridged by linker groups to form a "oligomer" type structure, which may be linear or cyclic. Alternatively, the ligand moieties of formulae I and/or II may be joined in a "cross" or "star" topography to a central atom or group, each by a linker (e.g. "$R_L$" moiety). Linker ($R_L$) moieties may join solely through carbon-carbon bonds, or may attach to each other, to other chelating groups, to a backbone, template, coupling moiety or other linker by any appropriately robust functionality including an amine, amide, ester, ether, thio-ether or disulphide bond.

A "stellar" arrangement is indicated in formula III below:

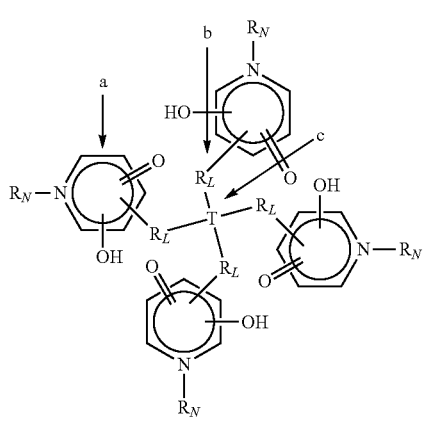

III

Wherein all groups and positions are as indicated above and "T" is additionally a central atom or template group, such as a carbon atom, hydrocarby chain (such as any of those described herein above), aliphatic or aromatic ring (including heterocyclic rings) or fused ring system. The most basic template would be a single carbon, which would then attach to each of the chelating moieties by their linking groups. Longer chains, such as ethyl or propyl are equally viable with two chelating moieties attaching to each end of the template. Evidently, any suitably robust linkage may be used in joining the template and linker moieties including carbon-carbon bonds, ester, ether, amine, amide, thio-ether or disulphide bonds.

In the structure of formula III groups $R_N$ and $R_L$ may be the same group such that the chelating moieties attach to the template T through the nitrogen atom of the pyridine ring. This provides structures of type IIIb below:

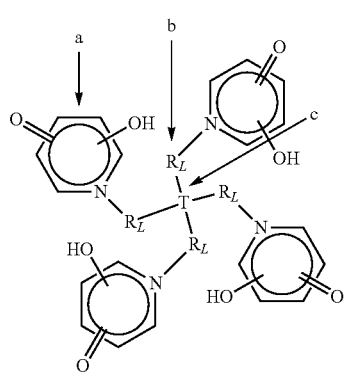

IIIb

Evidently, in the structures of formula II III, IIIb, IV and IVb, those positions of the pyridine ring(s) which are not otherwise substituted (e.g by a linker or coupling moiety) may carry substituents described for $R_1$ to $R_5$ in Formula I, as appropriate. In particular, small alkyl substituents, such as methyl, ethyl or propyl groups may be present at any position.

The octadentate ligand will generally additionally comprise at least one coupling moiety as described above. This may be any suitable structure including any of those indicated herein and will terminate with the targeting moiety, a specific binder or a functional group capable of linking to such a targeting moiety or specific binder.

The coupling moiety may attach to any suitable point of the linker, template or chelating moiety, such as at points a), b) and/or c) as indicated in formula III. The attachment of the coupling moiety may be by any suitably robust linkage such as carbon-carbon bonds, ester, ether, amine, amide, thio-ether or disulphide bonds. Similarly, groups capable of forming any such linkages to the targeting moiety are suitable for the functional end of the coupling moiety and that moiety will terminate with such groups when attached to the targeting part.

An alternative, "backbone" type structure is indicated below in Formula IV

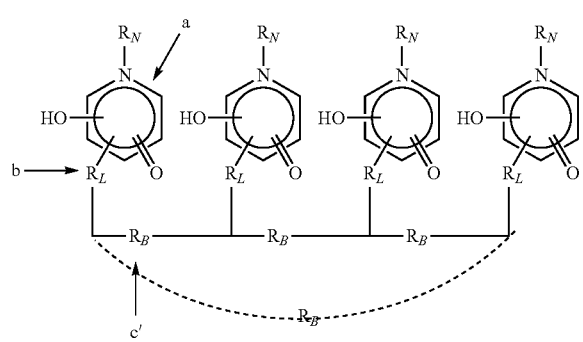

IV

Wherein all groups and positions are as indicated above and "$R_B$" is additionally a backbone moiety, which will typically be of similar structure and function to any of the linker moieties indicated herein, and thus any definition of a linker moiety may be taken to apply to the backbone moiety where context allow. Suitable backbone moieties will form a scaffold upon which the chelating moieties are attached by means of their linker groups. Usually three or four backbone moieties are required. Typically this will be three for a linear backbone or four if the backbone is cyclised. Particularly preferred backbone moieties include short hydrocarbon chains (such as those described herein) optionally having a heteroatom or functional moiety at one or both ends. Amine and amide groups are particularly suitable in this respect.

The coupling moiety may attach to any suitable point of the linker, backbone or chelating moiety, such as at points a), b) and/or c') as indicated in formula IV. The attachment of the coupling moiety may be by any suitably robust linkage such as carbon-carbon bonds, ester, ether, amine, amide, thio-ether or disulphide bonds. Similarly, groups capable of forming any such linkages to the targeting moiety are suitable for the functional end of the coupling moiety and that moiety will terminate with such groups when attached to the targeting part.

As with Formula III, in the structure of formula IV groups $R_N$ and $R_L$ may be the same group such that the chelating moieties attach to the Backbone $R_B$ through the nitrogen atom of the pyridine ring. This provides structures of type IVb below:

IVb

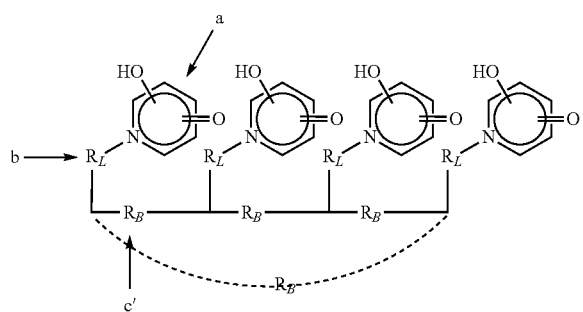

An example of a "backbone" type octadentate ligand having two 1,2 and two 3,2-HOPO chelating moieties attached to a backbone by amide linker groups would be formula V as follows:

V

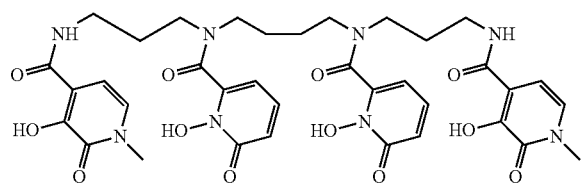

Exemplary "templated" octadentate ligands, each having four 3,2-HOPO chelating moieties linked by ethyl amide groups to ethyl and propyl diamine respectively would be formulae VI and VII as follows:

VI

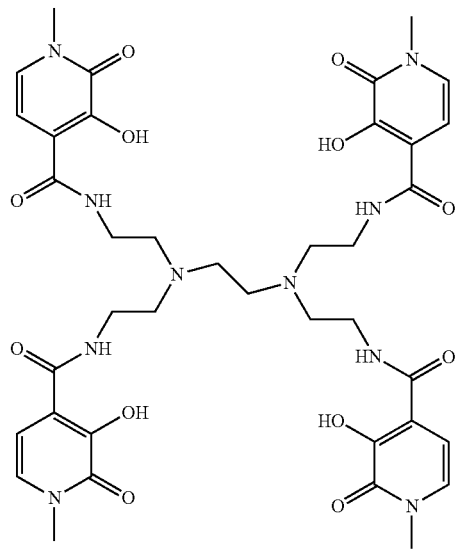

VII

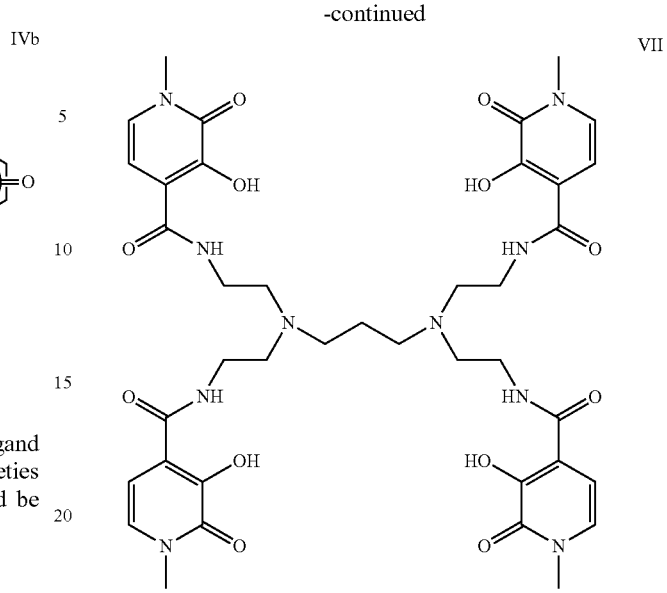

It will be noted that in the above formulae, the free nitrogens of the 3,2-HOPO moieties are substituted with methyl groups and small hydrocarbyl groups such as methyl or ethyl are preferable at this position ($R_1$ in Formula I or $R_N$ in formula II).

An exemplary "templated" octadentate ligands, having four 3,2-HOPO chelating moieties linked by the nitrogen in the HOPO ring to the amine cyclane would be formulae VIII as follows:

VIII

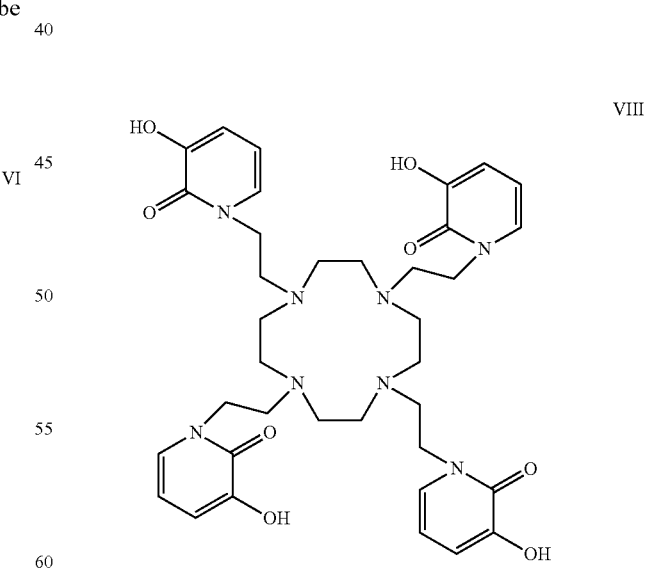

As indicated above, the octadentate ligand will typically include a coupling moiety which may join to the remainder of the ligand at any point. An exemplary compound with a functionalized moiety terminating the coupling moiety, according to this embodiment, is structure IX below:

IX

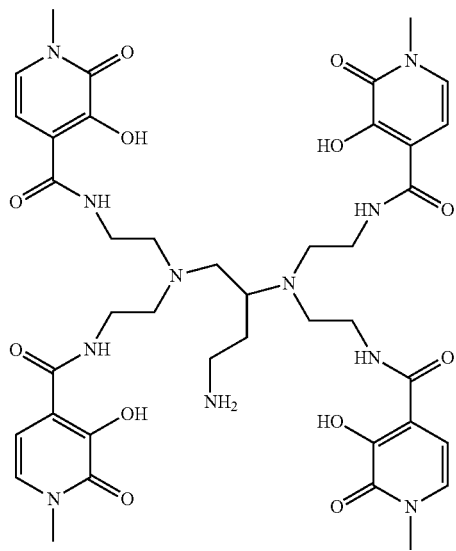

All documents referred to herein are hereby incorporated by reference, including Gordon AEV et al, Rational design of sequestering agents for plutonium and other actinides. Chem. Rev. 2003, 103, 4207-4282, PCT Patent Application WO 2008/063721 A2 and T. N. Lambert et al., Tetrahedron Letters 43 (2002) 7379-7383.

The invention is further illustrated by the attached Figures, in which:

DETAILED DESCRIPTION OF THE INVENTION

Figure 1:
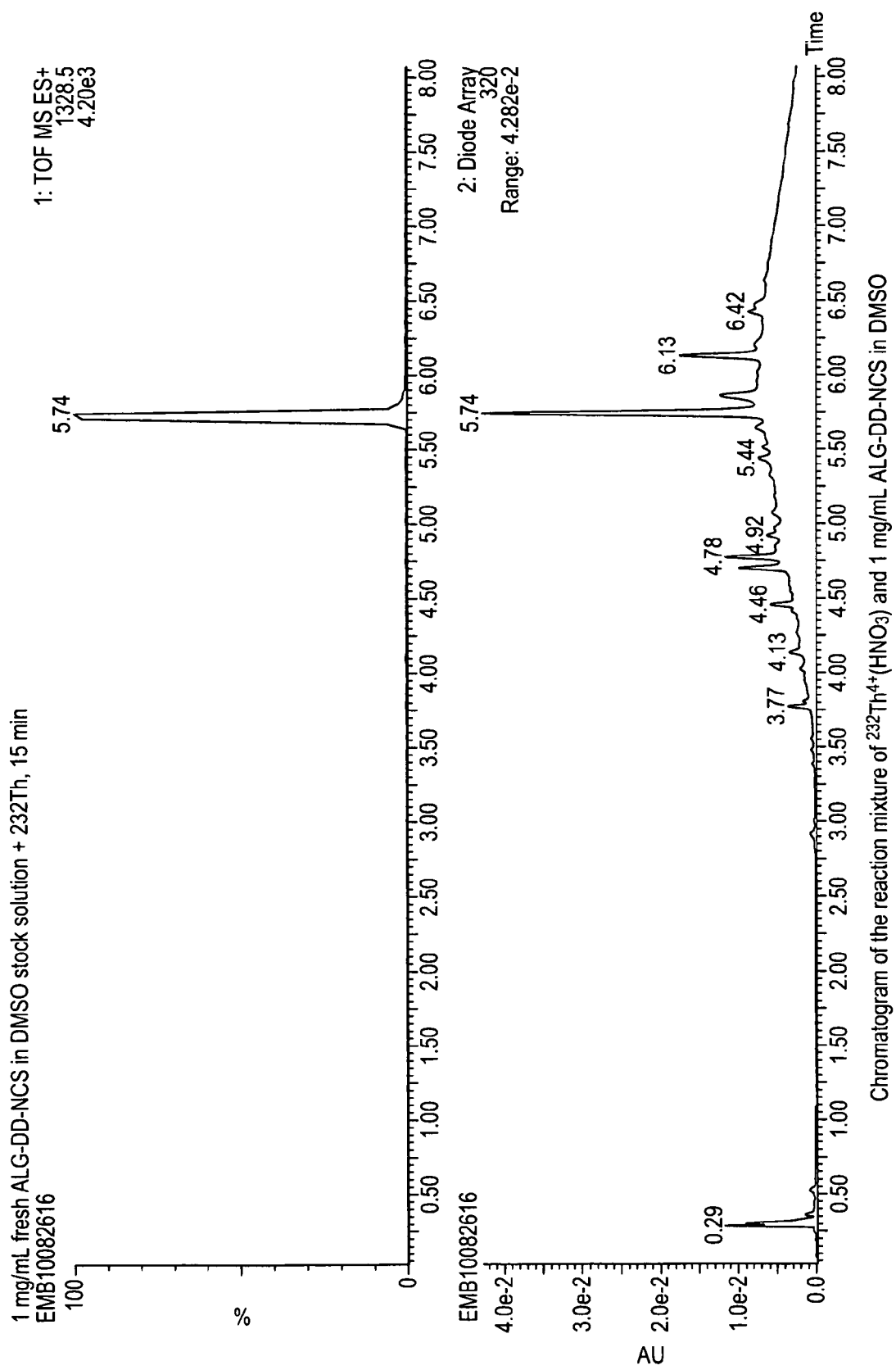
FIG. 1—shows the chromatogram of the reaction mixture of $^{232}Th^{4+}$ (HNO$_3$) and 1 mg/mL ALG-DD-NCS in DMSO (theoretical ratio 2:3) after 15 minutes at RT. There are significant amounts of the complex $^{232}$Th-ALG-DD-NCS ($t_R$=5.74 min; m/z 1328.5), and no traces of the free ALG-DD-NCS ligand ($t_R$=5.36).
Figure 2:
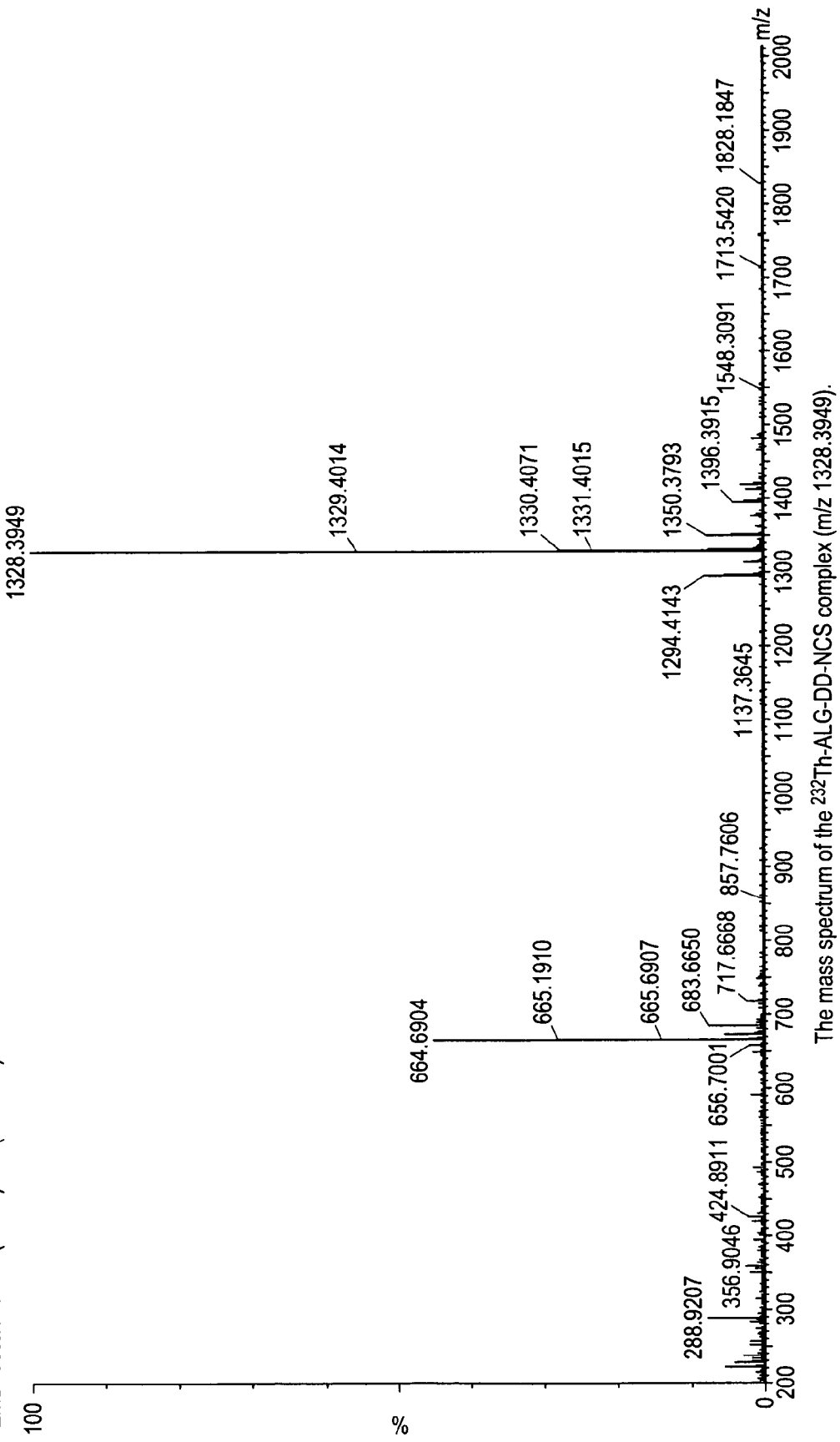
FIG. 2—shows the mass spectrum of the $^{232}$Th-ALG-DD-NCS complex (m/z 1328.3949).
Figure 3:
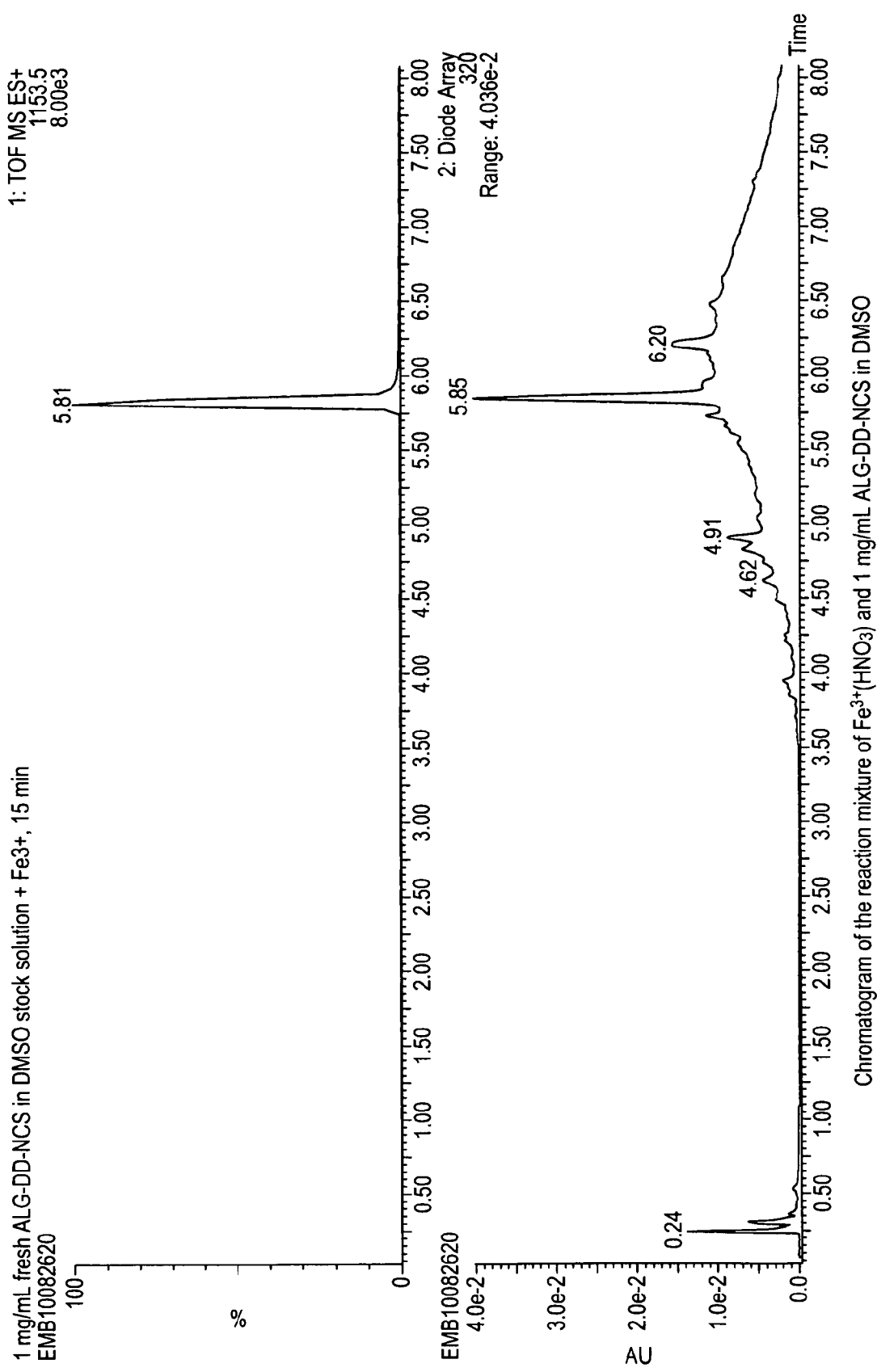
FIG. 3—shows the chromatogram of the reaction mixture of $Fe^{3+}$ (HNO$_3$) and 1 mg/mL ALG-DD-NCS in DMSO (theoretical ratio 2:3) after 15 minutes at RT. There are significant amounts of the complex Fe-ALG-DD-NCS ($t_R$=5.81 min; m/z 1153.5), and no traces of the free ALG-DD-NCS ligand ($t_R$=5.36 min).
Figure 4:
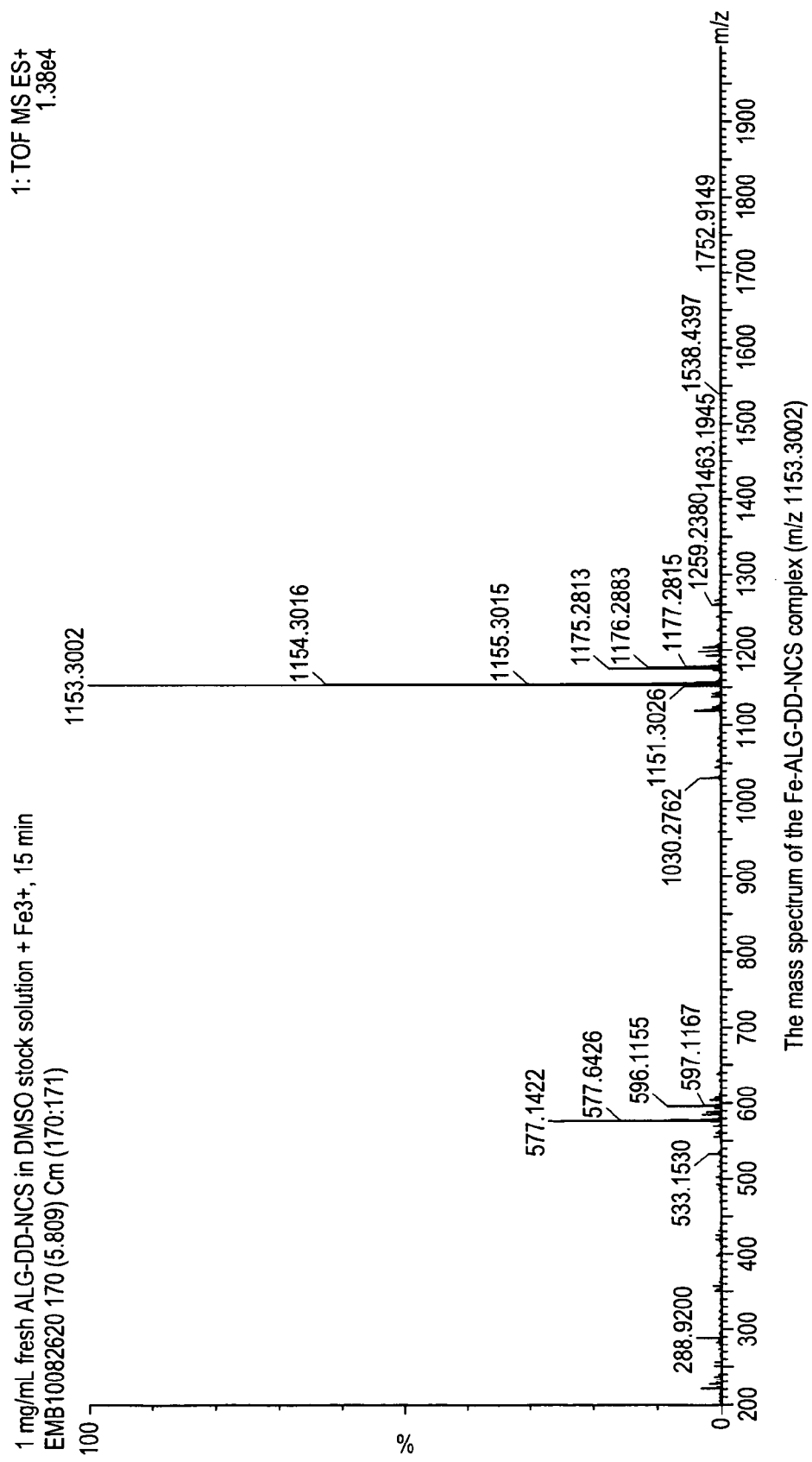
FIG. 4—shows the mass spectrum of the Fe-ALG-DD-NCS complex (m/z 1153.3002).
Figure 5:
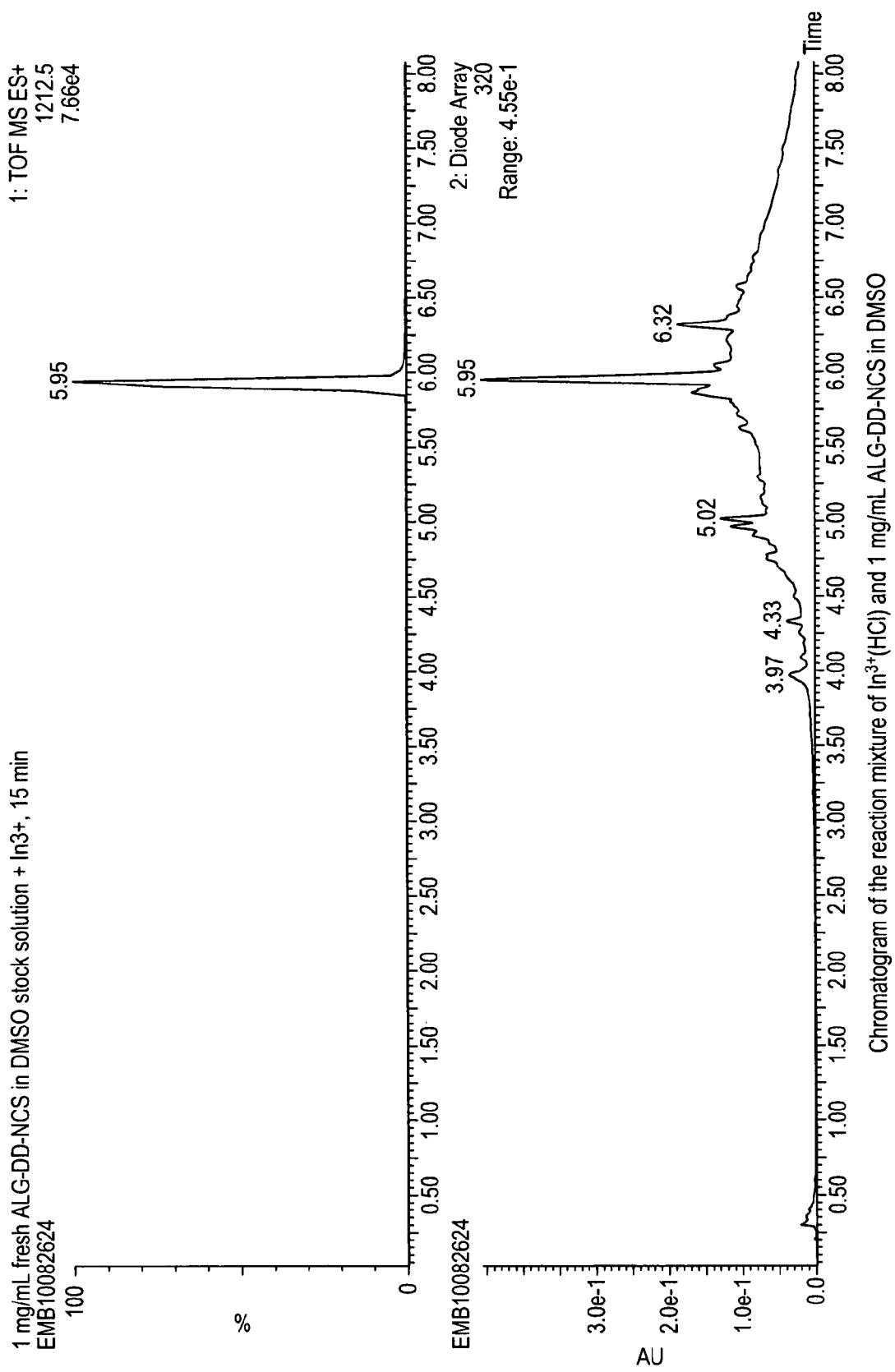
FIG. 5—shows the chromatogram of the reaction mixture of $In^{3+}$ (HCl) and 1 mg/mL ALG-DD-NCS in DMSO (theoretical ratio 2:3) after 15 minutes at RT. There are significant amounts of the complex In-ALG-DD-NCS ($t_R$=5.95 min; m/z 1212.5), and no traces of the free ALG-DD-NCS ligand ($t_R$=5.36 min).
Figure 6:
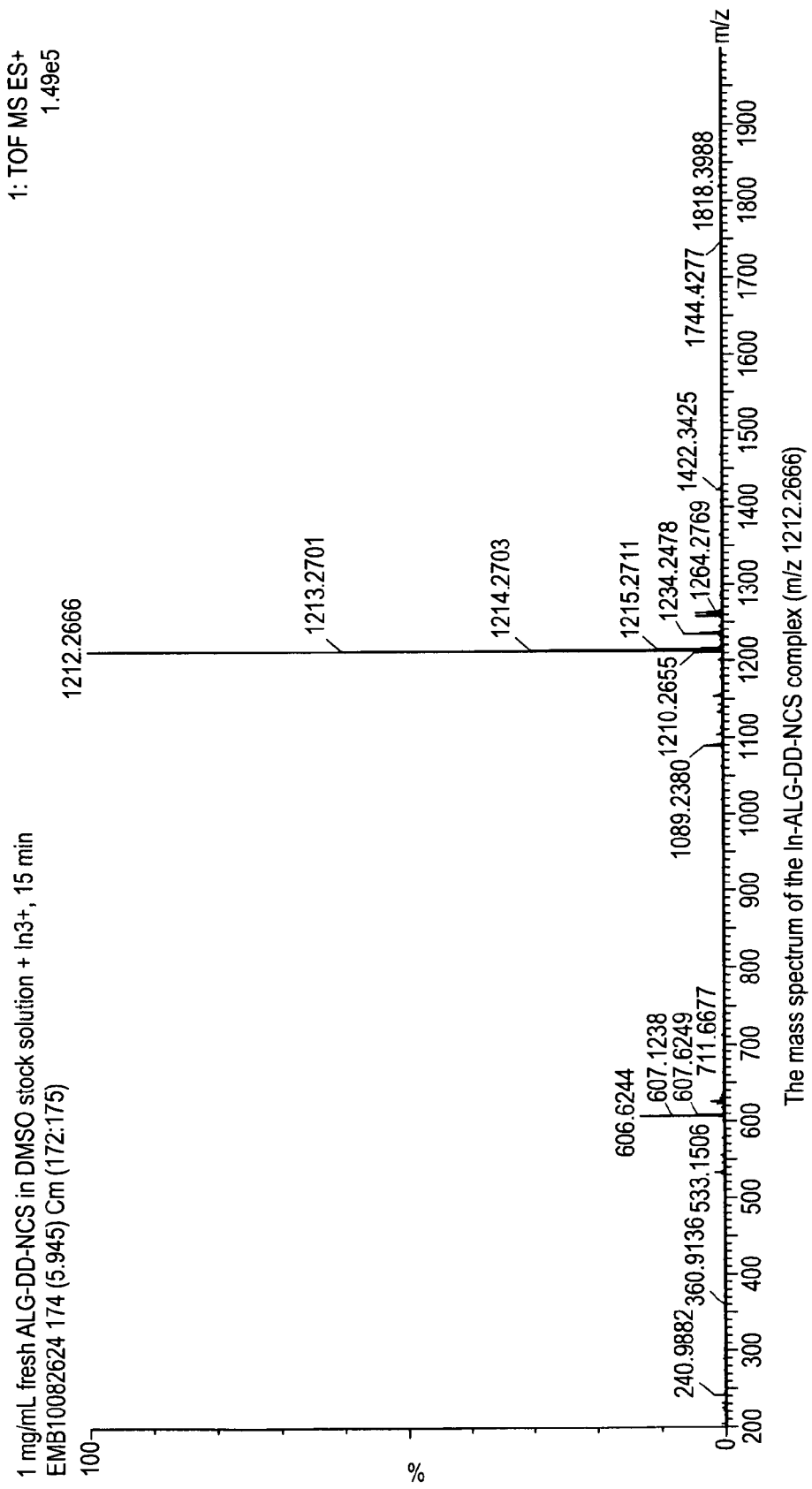
FIG. 6:—shows the mass spectrum of the In-ALG-DD-NCS complex (m/z 1212.2666).
Figure 7:
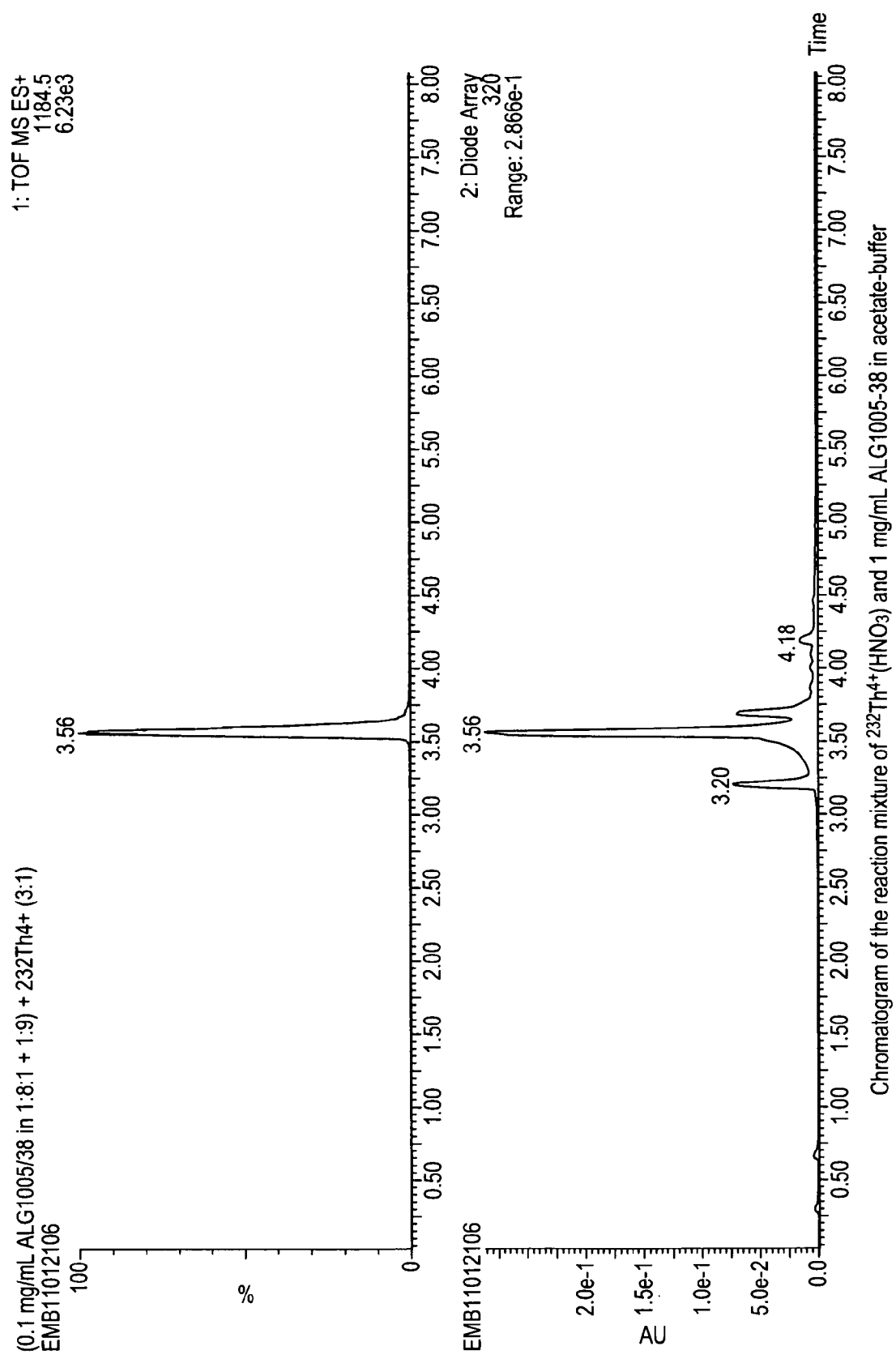
FIG. 7—shows the chromatogram of the reaction mixture of $^{232}Th^{4+}$ (HNO$_3$) and 1 mg/mL ALG1005-38 in acetate-buffer, pH 5.5, after 10 minutes at RT (theoretical ratio 1:3). There are significant amounts of the complex $^{232}$Th-ALG1005-38 ($t_R$=3.56; m/z 1184.5) and residues of the free ALG1005-38 ligand ($t_R$=3.20).
Figure 8:
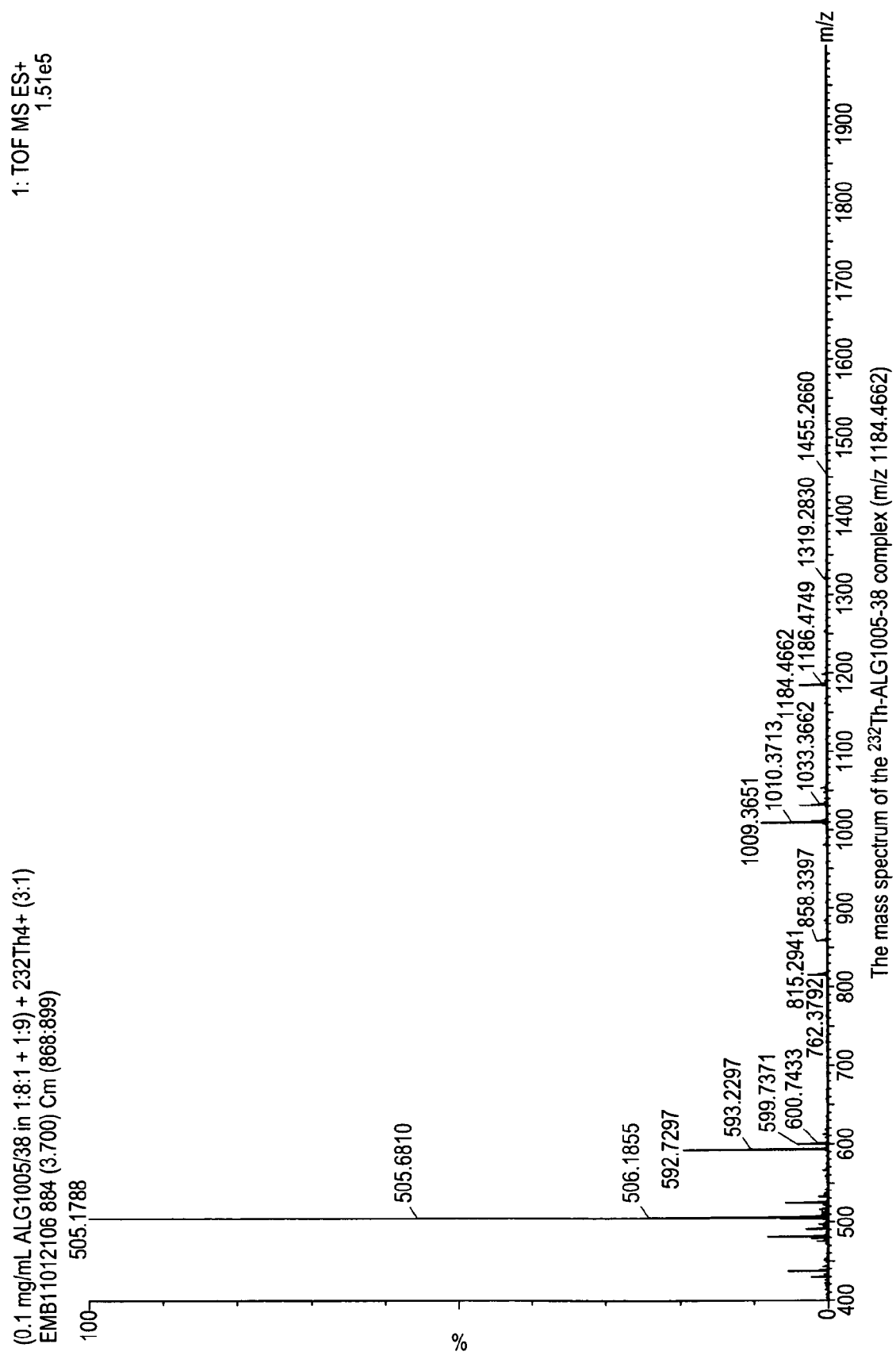
FIG. 8—shows the mass spectrum of the $^{232}$Th-ALG1005-38 complex (m/z 1184.4662).
Figure 9:
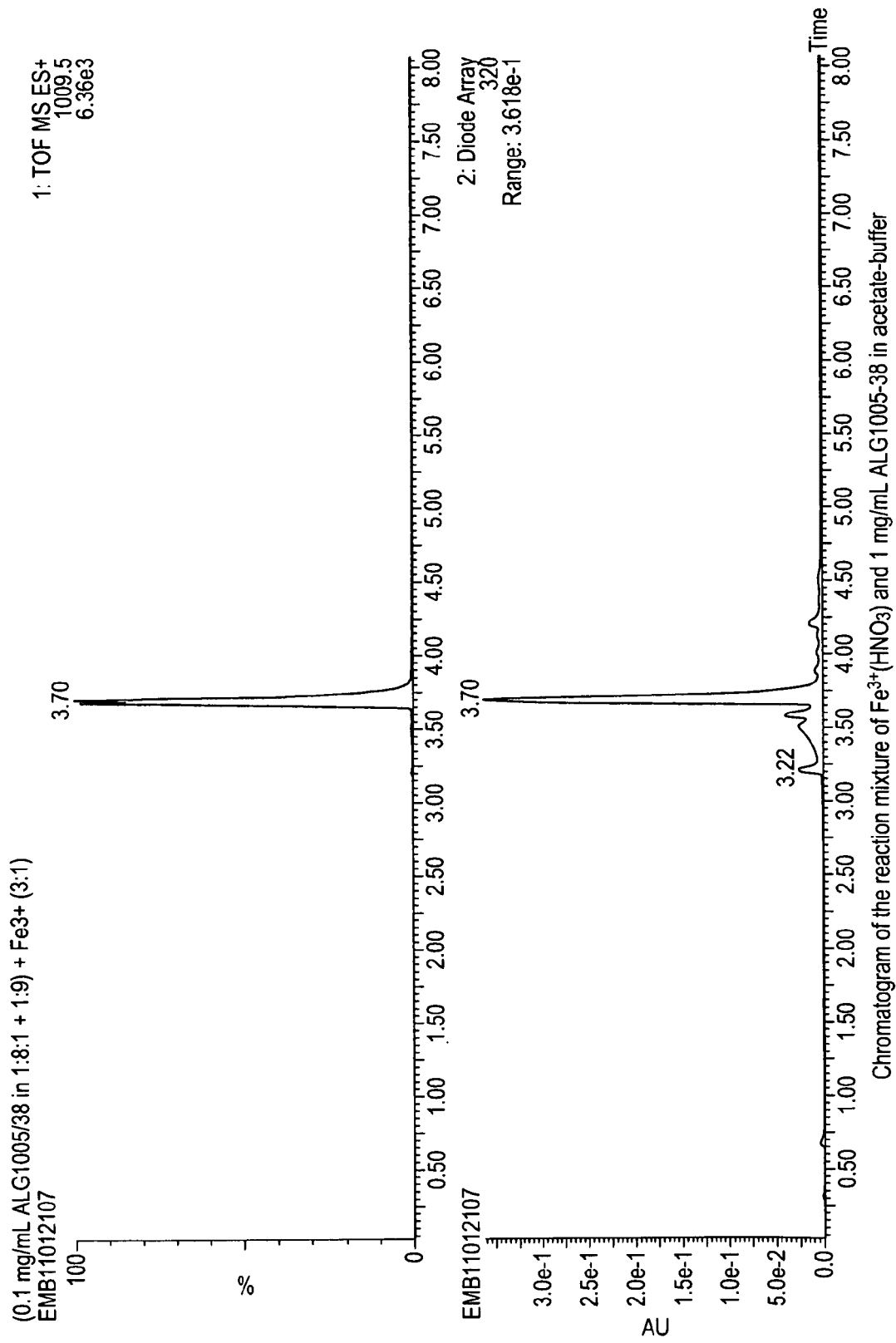
FIG. 9—shows the chromatogram of the reaction mixture of $Fe^{3+}$ (HNO$_3$) and 1 mg/mL ALG1005-38 in acetate-buffer, pH 5.5, after 10 minutes at RT (theoretical ratio 1:3). There are significant amounts of the complex Fe-ALG1005-38 ($t_R$=3.70; m/z 1009.5) and residues of the free ALG1005-38 ligand ($t_R$=3.22).
Figure 10:
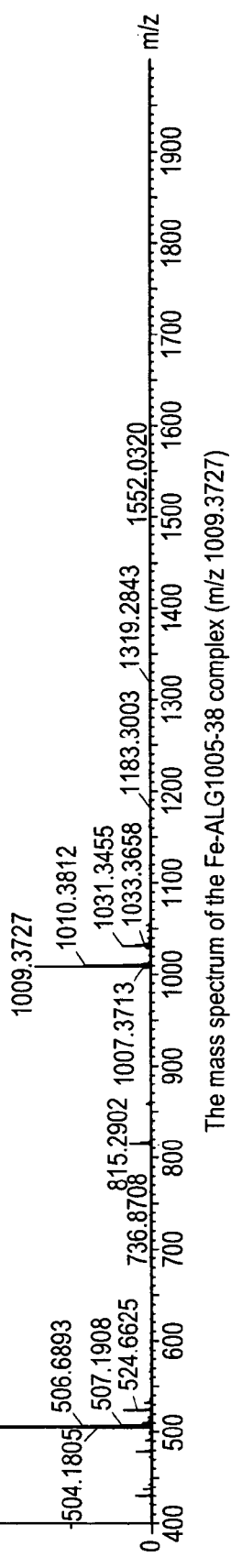
FIG. 10—shows the mass spectrum of the Fe-ALG1005-38 complex (m/z 1009.3727).
Figure 11:
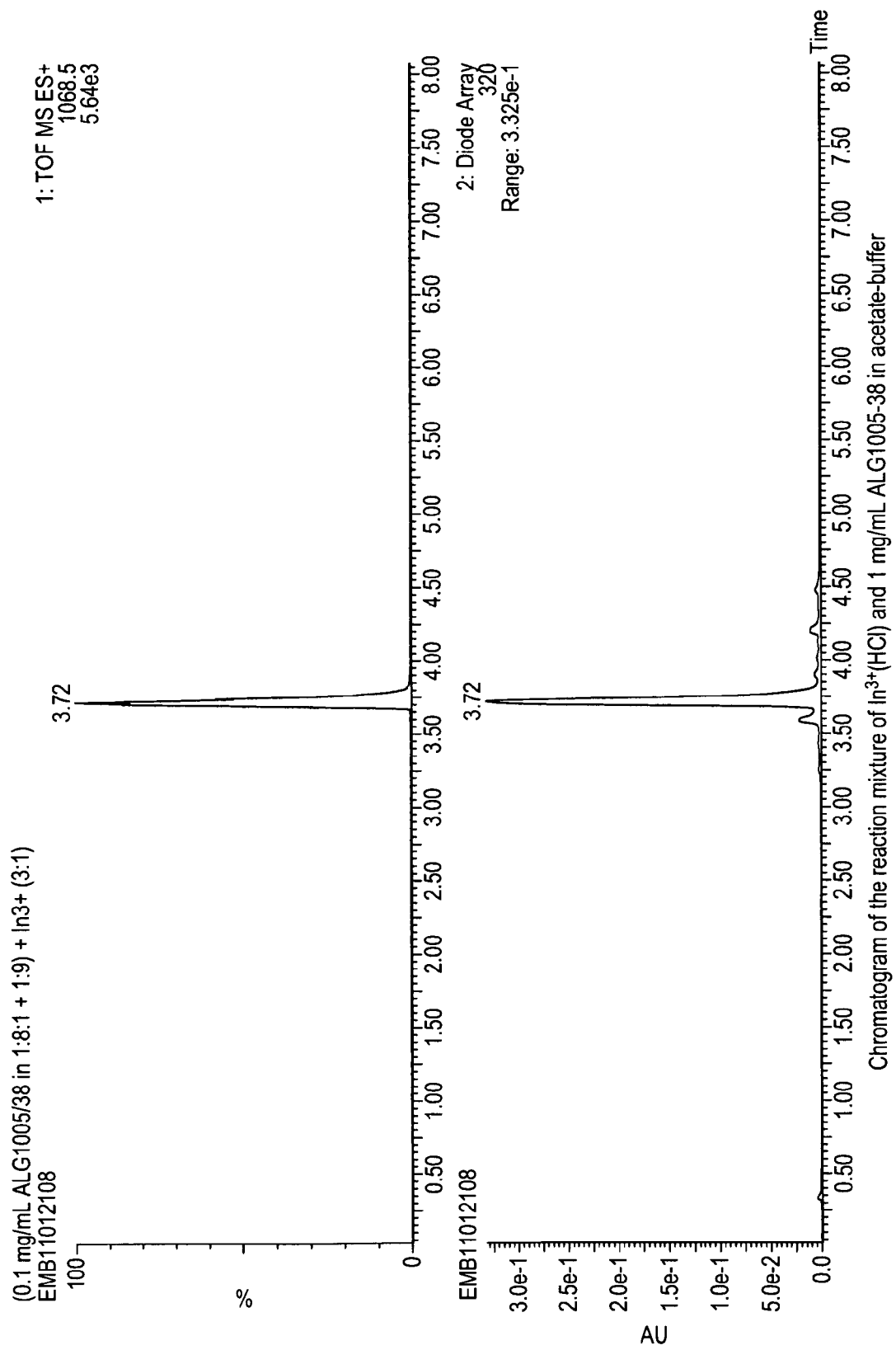
FIG. 11—shows the chromatogram of the reaction mixture of $In^{3+}$ (HCl) and 1 mg/mL ALG1005-38 in acetate-buffer, pH 5.5, after 10 minutes at RT (theoretical ratio 1:3). There are significant amounts of the complex In-ALG1005-38 ($t_R$=3.72; m/z 1068.5) and only traces of the free ALG1005-38 ligand ($t_R$=3.21).
Figure 12:
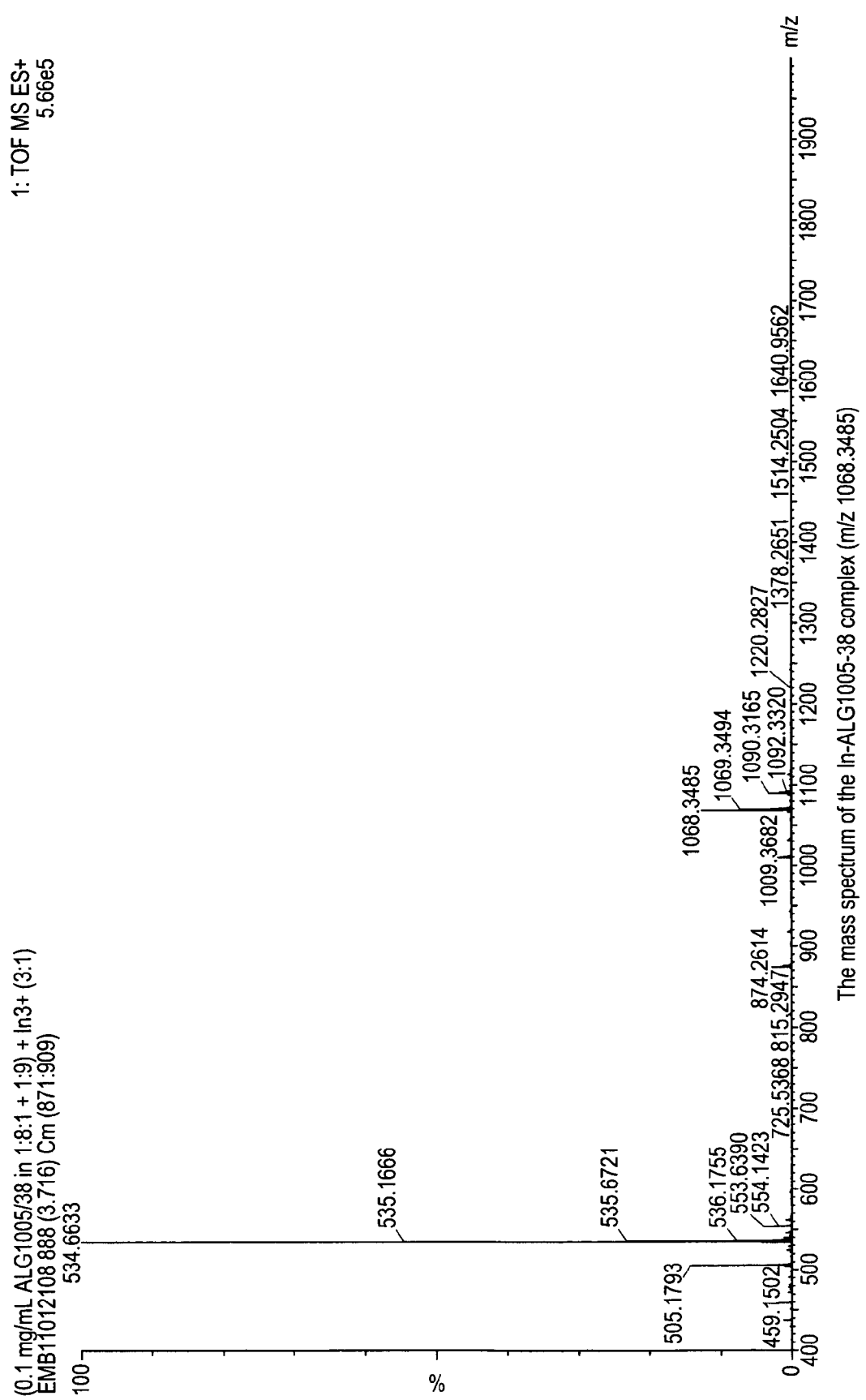
FIG. 12—shows the mass spectrum of the In-ALG1005-38 complex (m/z 1068.3485).
Figure 13:
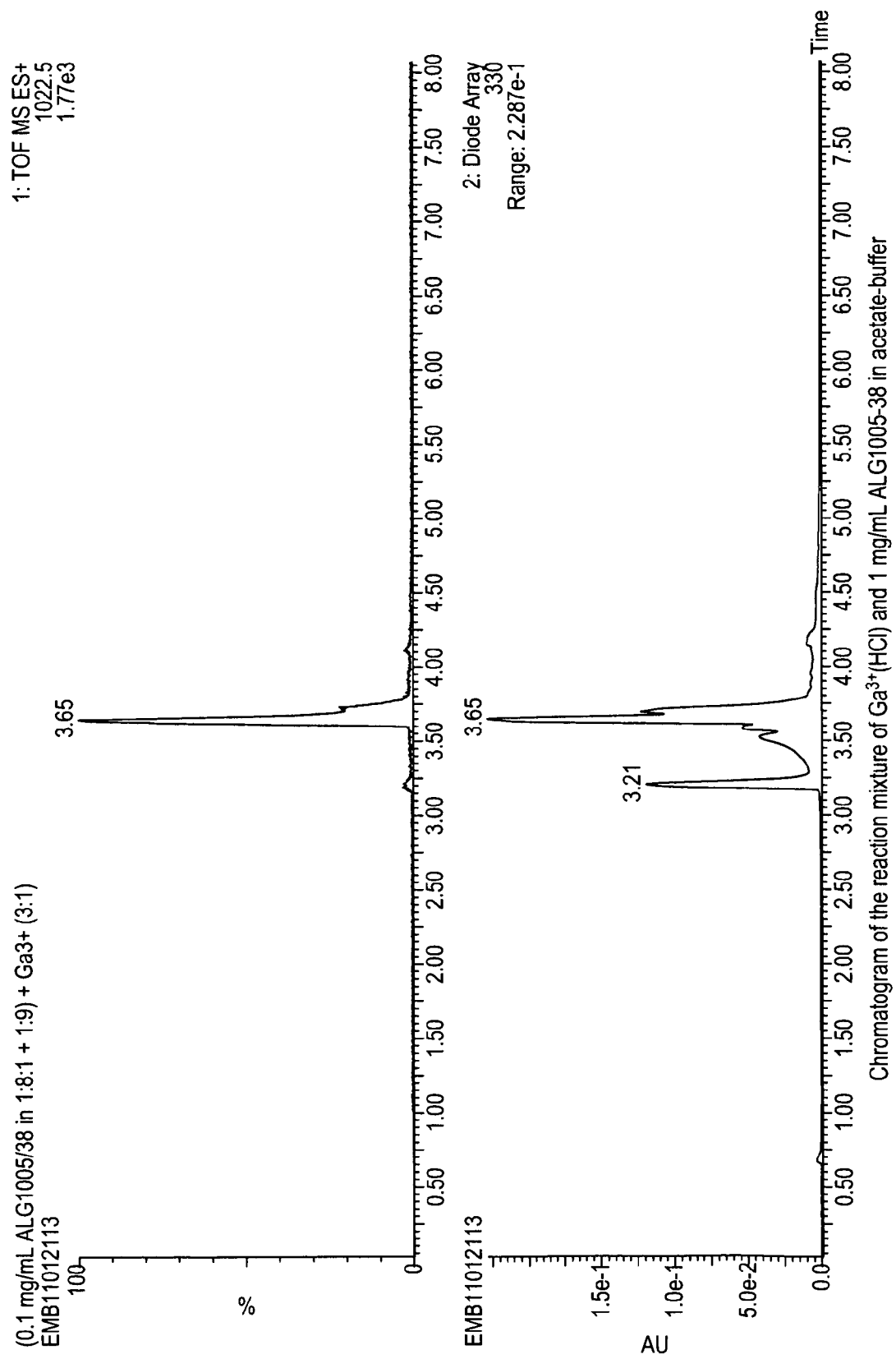
FIG. 13—shows the chromatogram of the reaction mixture of $Ga^{3+}$ (HCl) and 1 mg/mL ALG1005-38 in acetate-buffer, pH 5.5, after 10 minutes at RT (theoretical ratio 1:3). Significant amounts of the complex Ga-ALG1005-38 ($t_R$=3.65; m/z 1022.5) and residues of the free ALG1005-38 ligand ($t_R$=3.21).
Figure 14:
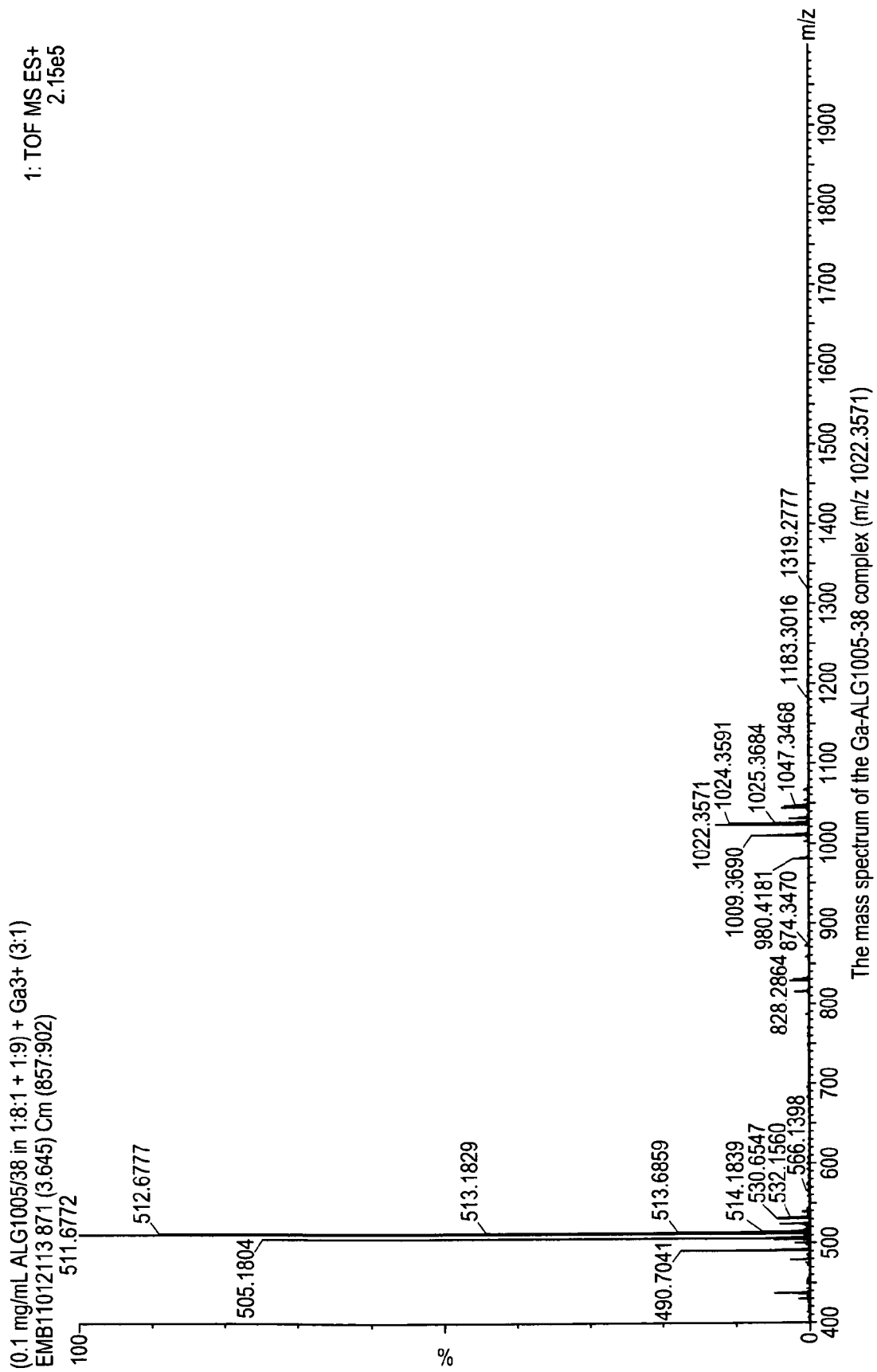
FIG. 14—shows the mass spectrum of the Ga-ALG1005-38 complex (m/z 1022.3571).

The invention will now be illustrated by the following non-limiting Examples. All compounds exemplified in the examples form preferred embodiments of the invention (including preferred intermediates and precursors) and may be used individually or in any combination in any aspect where context allows. Thus, for example, each and all of compounds 2 to 4 of Example 2, compound 10 of Example 3 and compound 7 of Example 4 form preferred embodiments of their various types.

Example 1—Isolation of Pure Thorium-227

Thorium-227 is isolated from an actinium-227 cow. Actinium-227 was produced through thermal neutron irradiation of Radium-226 followed by the decay of Radium-227 ($t\frac{1}{2}$=42.2 m) to Actinium-227. Thorium-227 was selectively retained from an Actinium-227 decay mixture in 8 M $HNO_3$ solution by anion exchange chromatography. A column of 2 mm internal diameter, length 30 mm, containing 70 mg of AG® 1-X8 resin (200-400 mesh, nitrate form) was used. After Actinium-227, Radium-223 and daughters had eluted from the column, Thorium-227 was extracted from the column with 12 M HCl. The eluate containing Thorium-227 was evaporated to dryness and the residue resuspended in 0.01 M HCl.

Example 2—Synthesis of ALG-DD-NCS

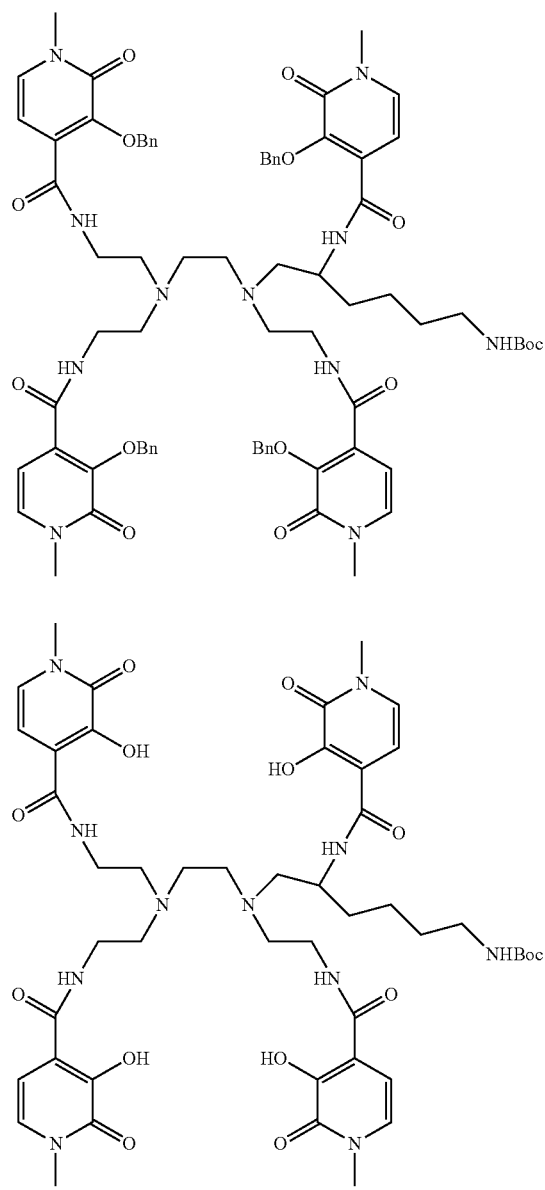

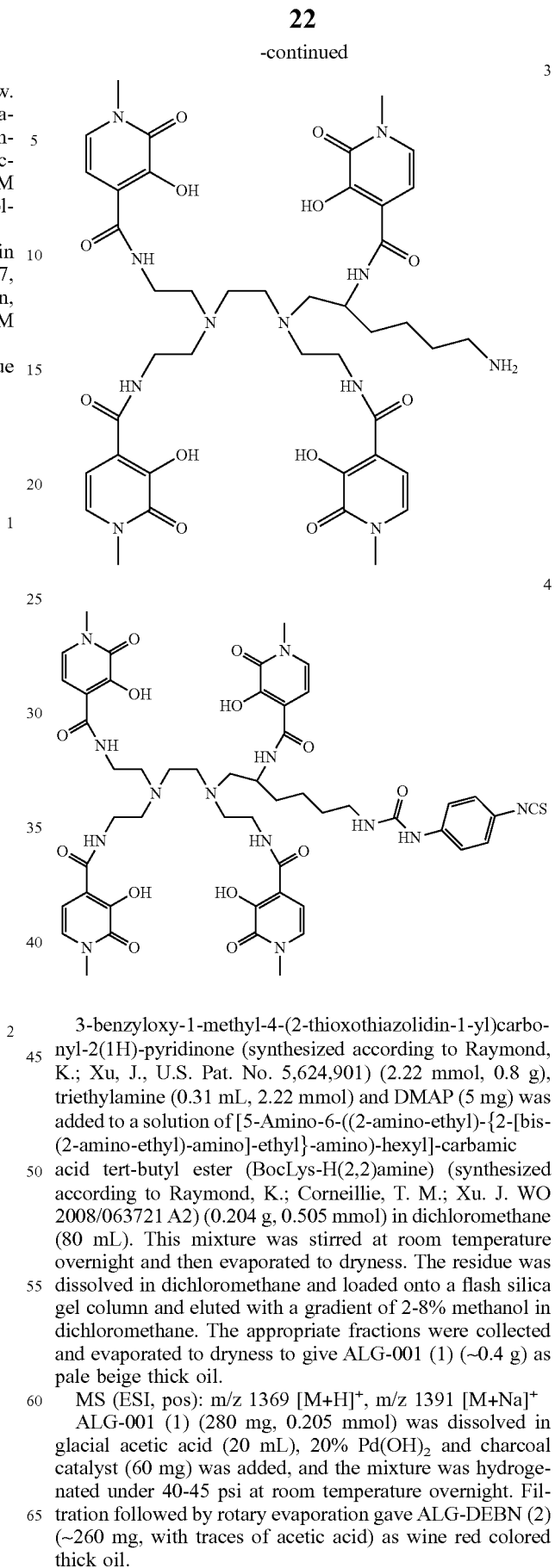

3-benzyloxy-1-methyl-4-(2-thioxothiazolidin-1-yl)carbonyl-2(1H)-pyridinone (synthesized according to Raymond, K.; Xu, J., U.S. Pat. No. 5,624,901) (2.22 mmol, 0.8 g), triethylamine (0.31 mL, 2.22 mmol) and DMAP (5 mg) was added to a solution of [5-Amino-6-((2-amino-ethyl)-{2-[bis-(2-amino-ethyl)-amino]-ethyl}-amino)-hexyl]-carbamic acid tert-butyl ester (BocLys-H(2,2)amine) (synthesized according to Raymond, K.; Corneillie, T. M.; Xu. J. WO 2008/063721 A2) (0.204 g, 0.505 mmol) in dichloromethane (80 mL). This mixture was stirred at room temperature overnight and then evaporated to dryness. The residue was dissolved in dichloromethane and loaded onto a flash silica gel column and eluted with a gradient of 2-8% methanol in dichloromethane. The appropriate fractions were collected and evaporated to dryness to give ALG-001 (1) (~0.4 g) as pale beige thick oil.

MS (ESI, pos): m/z 1369 [M+H]$^+$, m/z 1391 [M+Na]$^+$

ALG-001 (1) (280 mg, 0.205 mmol) was dissolved in glacial acetic acid (20 mL), 20% Pd(OH)$_2$ and charcoal catalyst (60 mg) was added, and the mixture was hydrogenated under 40-45 psi at room temperature overnight. Filtration followed by rotary evaporation gave ALG-DEBN (2) (~260 mg, with traces of acetic acid) as wine red colored thick oil.

MS (ESI, pos): m/z 1007 [M+H]+, m/z 1029 [M+Na]+

ALG-DEBN (2) (70 mg) was dissolved in 2:1 MeOH/dichloromethane (15 mL) at ambient temperature. Then 0.5 g of cleaned Amberlyst-15 resin was added, and the mixture was gently stirred overnight. The resin was then separated by filtration and washed with hexane (10 mL), tetrahydrofuran (10 mL), and methanol (10 mL), successively. This amine-bound resin was transferred to 4 M ammonia methanolic solution (20 mL) and was gently stirred for 50 min. Tetrahydrofuran (10 mL) was added, to dissolve all of the deprotected product. The resin was then removed by filtration, and the solution was evaporated, yielding ALG-DEBN-DEBOC (3) (37 mg).

MS (ESI, pos): m/z 909 [M+H]+, m/z 931 [M+Na]+

A suspension of 40 mg ALG-DEBN-DEBOC (3) in 6:1 isopropanol-water (v/v, 7 mL) was reacted with a solution of 1,4-phenylendiisothiocyanate (4.1 equiv.) in chloroform (2.5 mL). The reactants were stirred at room temperature for 30 minutes, when a sample was withdrawn for MS analysis. Peaks corresponding to the expected mass (1100) were observed. About 95 mg of a light brown solid was isolated after removal of the volatiles under vacuum. The light brown solid was suspended in acetonitrile, and the mixture heated under reflux for 15 min. The mixture was cooled down to room temperature, followed by isolation of 26 mg of ALG-DD-NCS (4) as brown solid by filtration.

Example 3—Synthesis of a Symmetric 3,2-HOPO Containing Chelator

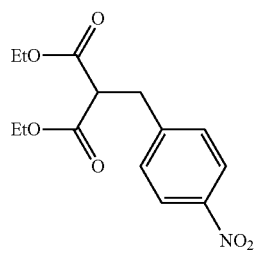

1

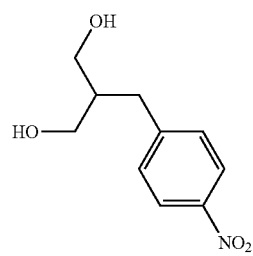

2

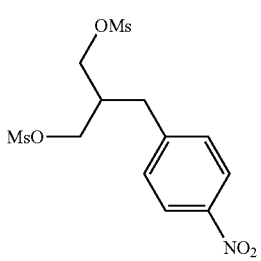

3

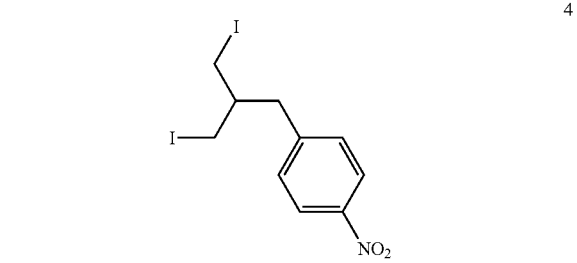

4

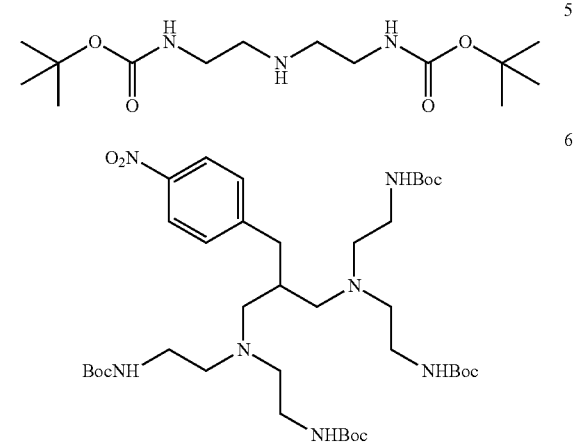

5

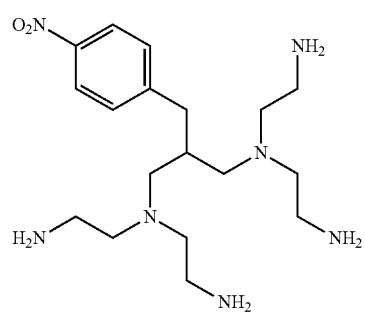

6

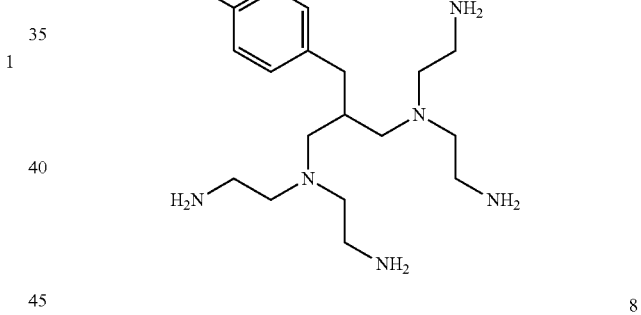

7

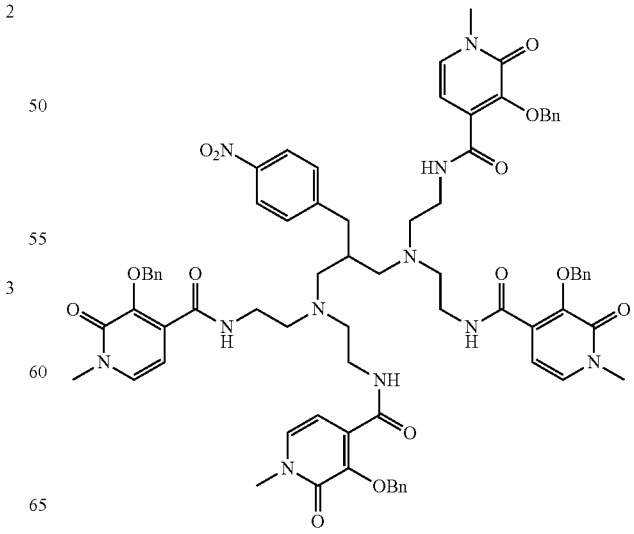

8

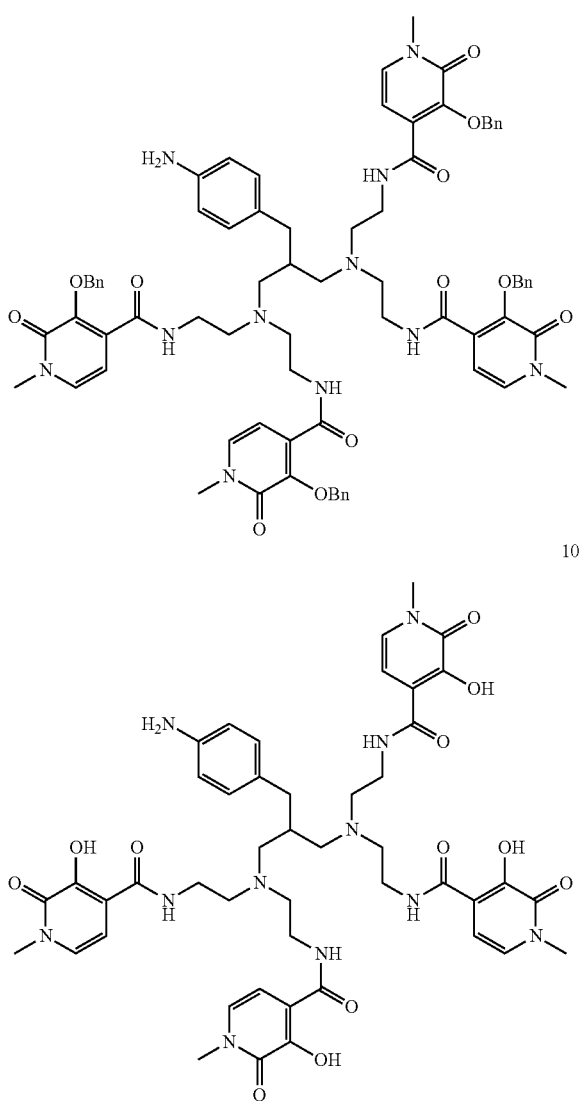

Sodium hydride (60.1 gas 60% dispersion in mineral oil, 1.5 mol, 5 eq.) was charged in a flask and tetrahydrofuran (1 L) was added. Dimethyl malonate (172 mL, 1.5 mol, 5 eq.) was added drop-wise over 1.5 h; the temperature of the reaction mixture was kept below +10° C. The reaction mixture was then diluted with tetrahydrofuran (400 mL). A solution of 4-nitrobenzyl bromide (65.0 g, 0.3 mol, 1 eq.) in tetrahydrofuran (170 mL) was slowly added over 30 min to the above-prepared mixture under vigorous shaking. After 30 min of stirring at 0° C., the reaction mixture was poured into brine (1 L saturated NaCl solution) and left stirring overnight at ambient temperature, yielding a white precipitate. The mixture was then diluted with methyl tert-butyl ether, and the precipitate was filtered off and dissolved in hot ethanol. The ethanolic mixture was filtrated, and the filtrate was concentrated to the small volume, from which 24.8 g (31%) of dimethyl (4-nitrobenzyl)propanedioate (1) precipitated as a white, crystalline solid.

LC Purity: >90% (254 nm)

MS (APCI pos) m/z 285.1 [M+NH$_4$]$^+$

Compound 1 (24.8 g, 92.7 mmol) was dissolved in tetrahydrofuran (230 mL) and added borane-dimethyl sulfide complex (28.5 mL, 301 mmol, 3.3 eq.). The reaction mixture was refluxed for 24 h, and then allowed to stand at ambient temperature overnight. Methanol (250 mL) was added at 0° C., poured into brine (600 mL) and extracted with ethyl acetate. The combined organic extracts were dried over Na$_2$SO$_4$ and concentrated in vacuo. The residue was co-evaporated with methanol.

The crude product was purified by flash chromatography, giving 14.5 g (74%) 2-(4-nitrobenzyl)propane-1,3-diol (2) as a yellow oil.

LC Purity: >92% (254 nm)

Compound 2 (10.0 g, 47.3 mmol) was dissolved in dichloromethane (100 mL) and added triethylamine (14.5 mL, 104 mmol, 2 eq.). The reaction mixture was cooled in an ice-bath and methanesulfonyl chloride (8.0 mL, 104 mmol, 2 eq.) was added in portions. The final mixture was allowed to reach ambient temperature overnight. Additional triethylamine (1.5 mL) and methanesulfonyl chloride (0.8 mL) were then added, and stirring was continued for 30 min. The reaction mixture was then diluted with dichloromethane, and the formed precipitate was filtered off. The dichloromethane filtrate was washed with saturated aqueous NaHCO$_3$ solution, 0.5 M aq. HCl and brine, dried over Na$_2$SO$_4$ and concentrated in vacuo, giving 14.5 g (83%) 2-(4-nitrobenzyl)propane-1,3-diyl dimethanesulfonate (3) as an orange oil, which was used in the next step without additional purification.

LC Purity: >87% (254 nm)

MS (APCI pos) m/z 385.3 [M+NH$_4$]$^+$

Compound 3 (14.5 g, 39.5 mmol) was dissolved in methyl ethyl ketone (100 mL), sodium iodide (16.0 g, 107 mmol, 2.7 eq.) was added, and the mixture was heated at 95° C. for 1 h. The resulting white precipitate was filtered off and washed with methyl ethyl ketone, and the filtrate was concentrated in vacuo. The crude product was triturated from methyl tert-butyl ether and purified by flash chromatography, giving 10.6 g (63%) 1-[3-iodo-2-(iodomethyl)propyl]-4-nitrobenzene (4) as a yellow solid.

LC Purity: >90% (254 nm)

MS (APCI pos) m/z 431.1 [M+H]$^+$

Diethylene triamine (10.8 mL, 100 mmol) and triethylamine (42 mL, 300 mmol, 3 eq.) were dissolved in tetrahydrofuran (500 mL) and cooled in ice-bath. A solution of Boc-ON (49.5 g, 200 mmol, 2 eq.) in tetrahydrofuran (190 mL) was then added drop-wise over 2.5 h. The reaction mixture was stirred at 0° C. for an additional 1 h, before it was allowed to reach ambient temperature over night. The reaction mixture was then concentrated in vacuo. The residue was dissolved in dichloromethane and washed with 1 M aq. NaOH. The organic phase was dried over Na$_2$SO$_4$ and concentrated in vacuo. The crude material was purified by flash chromatography, giving 20.0 g (66%) di-tert-butyl (iminodiethane-2,1-diyl)biscarbamate (5) as a yellow viscous oil.

MS (APCI pos) m/z 304.3 [M+H]$^+$

Compound 5 (26.0 g, 86 mmol, 4 eq.) was dissolved in dry toluene (40 mL) and added N-ethyl morpholine (5.4 mL, 42 mmol, 2 eq.). Compound 4 (9.2 g, 21 mmol) was dissolved in dry toluene (35 mL) and added to the reaction mixture. The mixture was incubated in a pressure reactor at 105° C. for 5 days. The reaction mixture was then cooled down to ambient temperature, diluted with ethyl acetate and washed with saturated aqueous NaHCO$_3$ solution. The combined organic extracts were washed with water and brine, dried over Na$_2$SO$_4$ and concentrated in vacuo. The crude product was purified by flash chromatography, yielding 11.4 g (70%) of compound 6 as a yellow solid foam.

LC Purity: >96% (210 nm)

MS (APCI pos) m/z 782.8, [M+H]+; 682.7 [M+H−Boc]+; 582.6 [M+H−2Boc]+; 382.1 [M+H−4Boc]+

Compound 6 (2.0 g, 2.6 mmol) was dissolved in dioxane (16 mL), and a 9 M solution of HCl in dioxane (22 mL) was added. The reaction mixture was stirred at ambient temperature overnight, and then concentrated to dryness in vacuo, giving 1.9 g of the HCl salt of compound 7 as a beige solid.

MS (APCI pos) m/z 382.5 [M+H]+

Compound 7 (1.9 g, 2.6 mmol) was added DMPU (1,3-dimethyl-3,4,5,6-tetrahydro-2(1H)-pyrimidinone) (9.5 mL) and 3-(benzyloxy)-1-methyl-4[(2-thioxo-1,3-thiazolidin-3-yl)carbonyl]pyridine-2-(1H)-one (3.7 g, 10.3 mmol, 4 eq.). A solution of DBU (2.3 mL, 15.5 mmol, 6 eq.) in DMPU (4.7 mL) was then added slowly over 40 min. Stirring was continued overnight at ambient temperature. The reaction mixture was then diluted with dichloromethane and washed with saturated aqueous NaHCO₃ solution. The combined organic extracts were washed with water and semi-saturated brine, then dried over Na₂SO₄ and concentrated in vacuo. The crude product was purified by flash chromatography to obtain 4.0 g of compound 8 as yellow oil that was used in the next step without additional purification.

MS (APCI pos) m/z 1347.7 [M+H]+

Compound 8 (4.0 g, 2.6 mmol) was dissolved in acetic acid (200 mL) and Pd(OH)₂ (20% w/w on C, 50% wetted) (800 mg, 10% w/w) was added. The reaction mixture was stirred in a Parr pressure reactor at 30 bar hydrogen pressure at ambient temperature overnight. The reaction mixture was then filtered through a pad of Celite®, and the filtrate was concentrated in vacuo. The crude product was purified by flash chromatography, giving compound 9 as a beige foamy solid.

Compound 9 (996 mg) was dissolved in acetic acid (5.5 mL), followed by addition of 6 M aqueous HCl (2.5 mL) and 5% Pd/C (99 mg, 10% w/w). The reaction mixture was stirred in a pressure reactor at 8 bar hydrogen pressure overnight, and then filtered through a pad of Celite®. The filtrate was concentrated in vacuo and co-evaporated with toluene and methanol. The residue was dissolved in methanol and precipitated by addition of diethyl ether. The formed beige precipitate was filtered off and dried in vacuo overnight, yielding 700 mg of the HCl salt of compound 10, ALG1005-38.

MS (APCI pos) m/z 956.7 [M+H]+

Example 4—Synthesis of an Alternative Symmetric 3,2-HOPO Containing Chelator

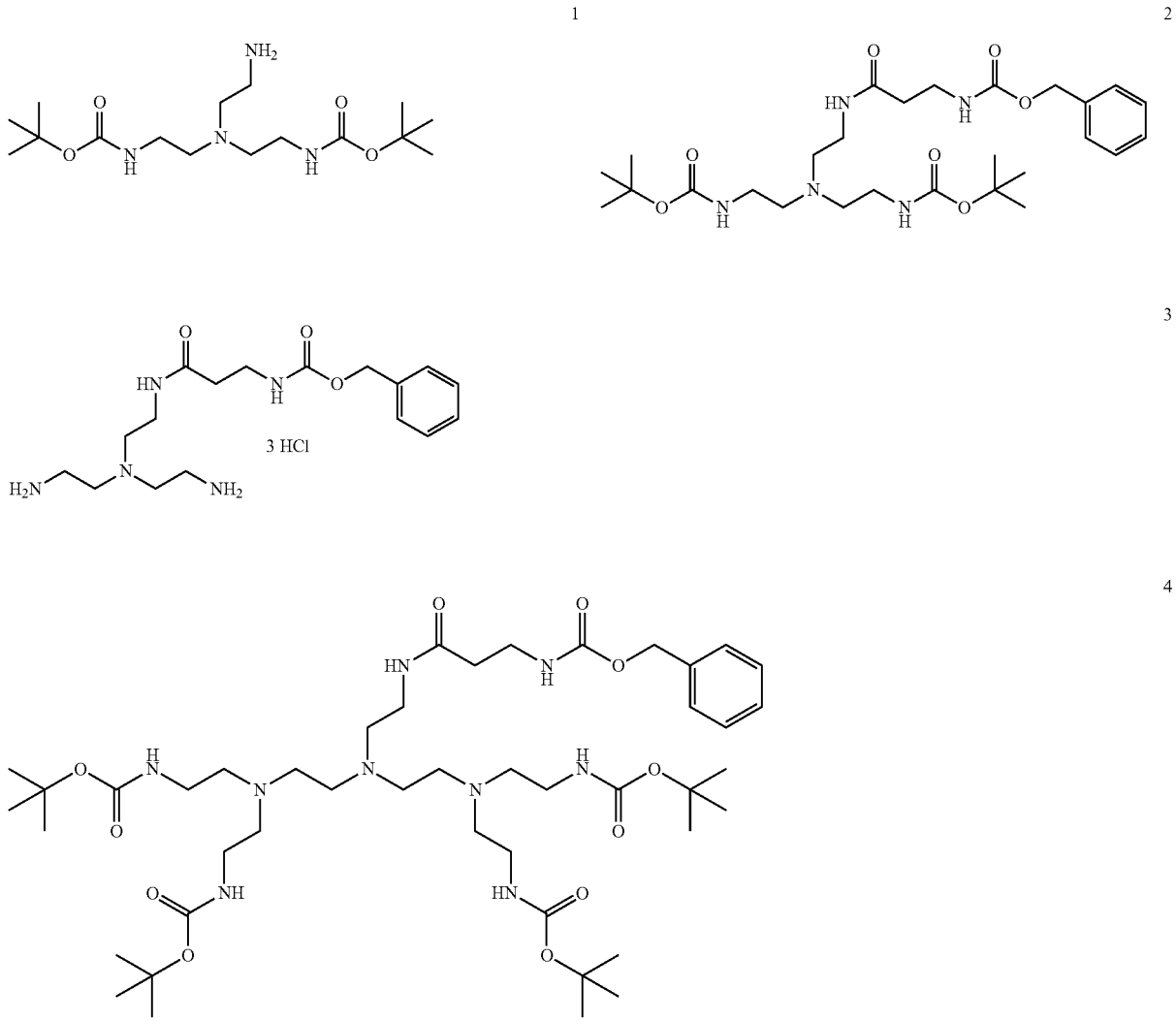

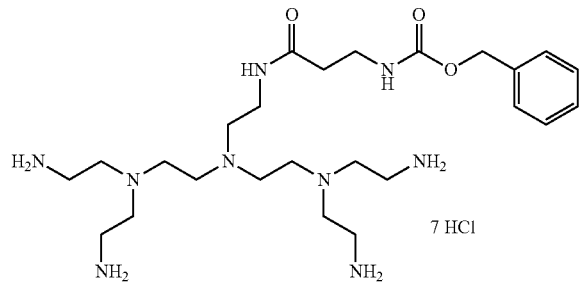

5

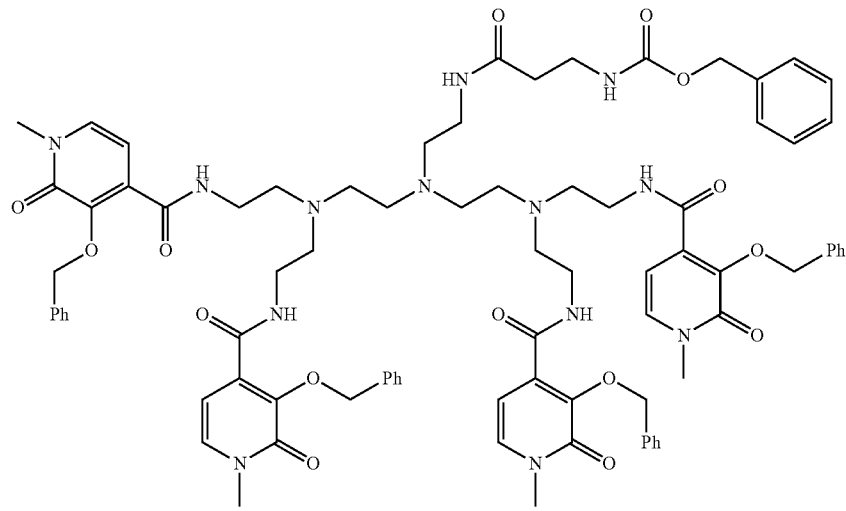

6

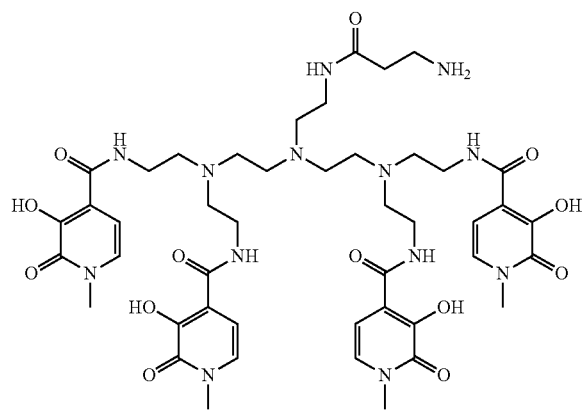

7

Boc anhydride (24.4 g, 119 mmol) was added in portions to a solution of imidazole (8.0 g, 117 mmol) in 50 mL dichloromethane at room temperature. The reaction mixture was stirred for one hour. The reaction mixture was washed twice with 50 mL water, dried over Na$_2$SO$_4$, filtered and reduced in vacuo. The residue was dissolved in 25 mL toluene and tris(2-aminoethyl)amine (8.19 g, 56 mmol) was added. The reaction mixture was stirred for 2 hours at 60° C. and reduced in vacuo. The residue was dissolved in 125 mL dichloromethane and washed with water (4 times with 50 mL), dried over Na$_2$SO$_4$, filtered and reduced in vacuo. Dry flash chromatography (0-15% methanol in dichloromethane with 1% triethylamine) yielded di-tert-butyl (((2-aminoethyl)azanediyl)bis(ethane-2,1-diyl))dicarbamate (1) (13.51 g, 39.0 mmol, 70%) as a thick colorless oil.

Spectroscopic data was in accordance with data reported by Frullano et al. (*Chem. Eur. J.* 2004, 10, 5205-17).

N-Cbz-β-alanine (8.04 g, 36 mmol), 4-(dimethylamino) pyridine (4.40 g, 36 mmol) and EDC.HCl (6.90 g, 36 mmol) was dissolved in 25 mL tetrahydrofuran and stirred for 10 minutes before Compound 1 (10.4 g, 30 mmol) dissolved in 75 mL tetrahydrofuran was added. The reaction mixture was stirred for 4 hours and reduced in vacuo. Purification by dry flash chromatography (0-40% tetrahydrofuran in dichloromethane) yielded di-tert-butyl (((2-(3-(Cbz-amino)propanamido)ethyl)azanediyl)bis(ethane-2,1-diyl)dicarbamate (2) (15.11 g, 27.4 mmol, 91%) as a very viscous slightly yellow oil.

$^1$H-NMR (300 MHz, CDCl$_3$): 1.43 (s, 18H), 2.42-2.56 (m, 8H), 3.04-3.17 (m, 4H), 3.19-3.32 (m, 2H), 3.41-3.57 (m, 2H), 5.08 (s, 2H), 5.22 (bs, 2H), 5.83 (bs, 1H), 7.23 (bs, 1H), 7.26-7.43 (m, 5H)

MS (ESI, pos): m/z 574.3 [M+Na]+ di-tert-butyl (((2-(3-(Cbz-amino)propanamido)ethyl)azanediyl)bis(ethane-2,1-diyl)dicarbamate (10.30 g, 18.7 mmol) was dissolved in 100 mL methanol and acetyl chloride (25 mL, 0.35 mol) was added drop wise. The reaction mixture was stirred for one hour at ambient temperature. The reaction mixture was reduced to approximately ⅓ of the volume in vacuo before 100 mL ether was added, leading to precipitation of a colorless solid. The solids were filtrated, washed with ether and dried in vacuo, giving benzyl (3-((2-(bis(2-aminoethyl)amino)ethyl)amino)-3-oxpropyl)carbamate tri-hydrochloride (3) (8.70 g, 18.7 mmol, ~100%) as a colorless solid.

$^1$H-NMR (300 MHz, MeOD): 3.19-3.28 (m, 2H), 3.38-3.62 (m, 14H), 5.10 (s, 2H), 7.26-7.39 (m, 5H)

MS (ESI, pos): m/z 352.2 [M+H]+

Triethylamine (6.75 mL, 48.4 mmol) was added to a suspension of Compound 3 (10.56 g, 11.4 mmol) in 320 mL tetrahydrofuran and 320 mL N,N-dimethylformamide at room temperature. N-boc-2-aminoacetaldehyde (16.0 g, 100.5 mmol) and sodium triacetoxyborohydride (32.00 g, 151 mmol) was added. The reaction mixture was stirred for 20 hours. 200 mL brine and 500 mL chloroform was added, the phases were separated, and the aqueous phase was extracted with 3×100 mL chloroform. The combined organic phases were washed with 100 mL brine, dried over $Na_2SO_4$, filtered and reduced in vacuo. Flash chromatography (0-10% methanol in dichloromethane) yielded tetra-tert-butyl (((((2-3-Cbz-aminopropanamido)ethyl)azanediyl)bis(ethane-2,1-diyl))bis(azanetriyl)tetrakis(ethane-2,1-diyl)tetracarbamate (4) (3.40 g, 3.7 mmol, 32%) as a yellow solid.

MS (ESI, pos): m/z 946.7 [M+Na]+

Compound 4 (3.40 g, 3.7 mmol) was dissolved in 60 mL methanol and acetyl chloride (12 mL, 0.17 mol) was added drop wise. The reaction was stirred at ambient temperature for one hour. The reaction mixture was reduced to approximately 10 mL in vacuo and 50 mL acetonitrile was added, leading to precipitation. The solid was filtered, washed with acetonitrile and dried in vacuo, giving benzyl (3-((2-(bis(2-aminoethyl)amino)ethyl)amino)ethyl)amino)-3-oxopropyl)carbamate hepta-hydrochloride (5) (2.88 g, 3.7 mmol, ~100%) as a colorless solid.

$^1$H-NMR (300 MHz, MeOD): 2.44-2.61 (m, 2H), 2.68-3.00 (m, 4H), 3.08-3.40 (m, 16H), 3.44-3.52 (m, 4H), 3.54-3.77 (m, 6H), 5.12 (s, 2H), 7.30-7.47 (m, 5H)

MS (ESI, pos): m/z 524.5 [M+H]+

Triethylamine (2.52 mL, 18.1 mmol) and 4-(dimethylamino)pyridine (12 mg, cat.) was added to a suspension of Compound 5 (0.81 g, 1.04 mmol) and 3-(benzyloxy)-1-methyl-4-(2-thioxothiazolidine-3-carbonyl)pyridine-2(1H)-one (1.50 g, 4.16 mmol) in 180 mL Dichloromethane. The reaction mixture was stirred over night and reduced in vacuo. Flash chromatography (0-10% methanol in dichloromethane) yielded benzyl (1-(3-(benzyloxy)-1-methyl-2-oxo-1,2-dihydropyridin-4-yl)-5-(2-(3-(benzyloxy)-1-methyl-2-oxo-1,2-dihydropyridine-4-carboxamido)ethyl)-8-(2-(bis(2-(3-(benzyloxy)-1-methyl-2-oxo-1,2-dihydropyridine-4-carboxamido)ethyl)amino)ethyl)-1,12-dioxo-2,5,8,11-tetraazatetradecan-14-yl)carbamate (6) (673 mg, 0.45 mmol, 43%) as a light brown solid.

$^1$H-NMR (300 MHz, $CDCl_3$): 2.10-2.40 (m, 20H), 3.02-3.21 (m, 10H), 3.32-3.46 (m, 2H), 3.50 (s, 12H), 4.99 (s, 2H), 5.25 (s, 8H), 5.95 (bs, 1H), 6.62 (d, 7.17 Hz, 4H), 7.01 (d, 7.17 Hz, 4H), 7.15-7.40 (m, 25H), 7.89 (bs, 4H)

$^{13}$C-NMR (75 MHz, $CDCl_3$): 11.48, 35.71, 37.18, 37.35, 37.50, 37.66, 46.18, 51.55, 52.15, 52.82, 53.28, 66.34, 74.64, 74.75, 77.43, 104.63, 127.90, 127.94, 128.40, 128.65, 128.75, 128.94, 130.81, 132.32, 136.27, 136.76, 146.19, 156.45, 159.51, 163.30, 171.31

MS (ESI, pos): m/z 766.9 [M+2Na]$^{2+}$

Compound 6 was dissolved and debenzylated essentially as described in Example 2, to yield Bb-1-HOPO-1-DEBN (7).

Example 5—Chelation Experiments with ALG-DD-NCS

A reaction solution was prepared by dissolving solid ALG-DD-NCS (4 in Example 2) in DMSO (Biotech grade solvent 99.8%) to 1 mg/mL.

Chelation reactions with different metals were conducted by mixing the 1 mg/mL reaction solution with selected metal solutions, using a ligand-to-metal ratio of 3:2. Metal ions for testing came from the following: $^{232}$Th-solution 2% $HNO_3$ (Perkin Elmer Pure Plus), $Fe^{3+}$-solution in 2% $HNO_3$ (Perkin Elmer Pure Plus), and $InCl_3$ (anhydrous powder 99.999+%, Aldrich) was dissolved in 0.01 M HCl. The reagents were allowed to react for 15 minutes at room temperature, before injecting 5 µL of the reaction mixture on a LC-MS for analysis.

The results showed that metal-ALG-DD-NCS complexes were formed quantitatively for the metals $^{232}$Th$^{4+}$, $Fe^{3+}$ and $In^{3+}$. LC-MS chromatograms and spectra of the $^{232}$Th-ALG-DD-NCS, Fe-ALG-DD-NCS and In-ALG-DD-NCS complexes are shown in FIGS. 1-6.

The LC-MS conditions were as follows: separation was done on a 1.7 µm, 2.1×50 mm Acquity UPLC BEH C18 column, at 50° C., using 0.05% formic acid in $H_2O$ as mobile phase A and 0.05% formic acid in acetonitrile as mobile phase B. The gradient composition and flow are shown in Table 3.

TABLE 3

| Time (min) | Flow (mL/min) | % A | % B |
|---|---|---|---|
| 0.0 | 0.6 | 95 | 5 |
| 2.0 | 0.6 | 95 | 5 |
| 9.0 | 0.8 | 40 | 60 |
| 9.1 | 0.8 | 10 | 90 |
| 10.0 | 0.8 | 10 | 90 |
| 10.1 | 0.8 | 95 | 5 |
| 11.4 | 0.8 | 95 | 5 |
| 11.5 | 0.6 | 95 | 5 |
| 12.0 | 0.6 | 95 | 5 |

Mass spectroscopic analysis was performed on a Xevo-ToF-1 instrument, using an acquisition mass range of ~450-1950 Da, a molarity ES+, a 3.0 kV capillary, scanning over 1.000 sec with a cone voltage of 20 V.

Example 6—Chelation Experiments with ALG1005-38

A stock solution was prepared by dissolving ALG1005-38 (10 in Example 3) in MeOH (LC-MS grade) to 10 mg/mL. The 10 mg/mL stock solution was diluted with MeOH and 0.5 M NaOAc-buffer (pH 5.5) in the proportions 1:8:1, to obtain a 1 mg/mL ALG1005-38 reaction solution. Chelation reactions with different metals were conducted by mixing the 1 mg/mL reaction solution with the selected metals, as specified in Example 5 and in addition $GaCl_3$ (anhydrous beads 99.99%, Aldrich) dissolved in 0.01 M HCl, giving ligand-to-metal ratios from 3:1 to 1:2. The reagents were allowed to react for 10 minutes at room temperature. Finally, the reaction mixtures were diluted 10-fold with formic acid (0.1%) before injecting 5 μL on a LC-MS for analysis. The LC-MS separation and analysis was performed as described in Example 5, except that the cone voltage was 35 V.

The results showed that metal-ALG1005-38 complexes were formed in significant amounts for metals like $^{232}Th^{4+}$, $Fe^{3+}$, $In^{3+}$ and $Ga^{3+}$. LC-MS chromatograms and spectra of the $^{232}$Th-ALG1005-38, Fe-ALG1005-38, In-ALG1005-38 and Ga-ALG1005-38 complexes are shown in FIGS. 7-14.

Example 7—Chelation Experiment with Bb-1-HOPO-1-DEBN

Figure 15:
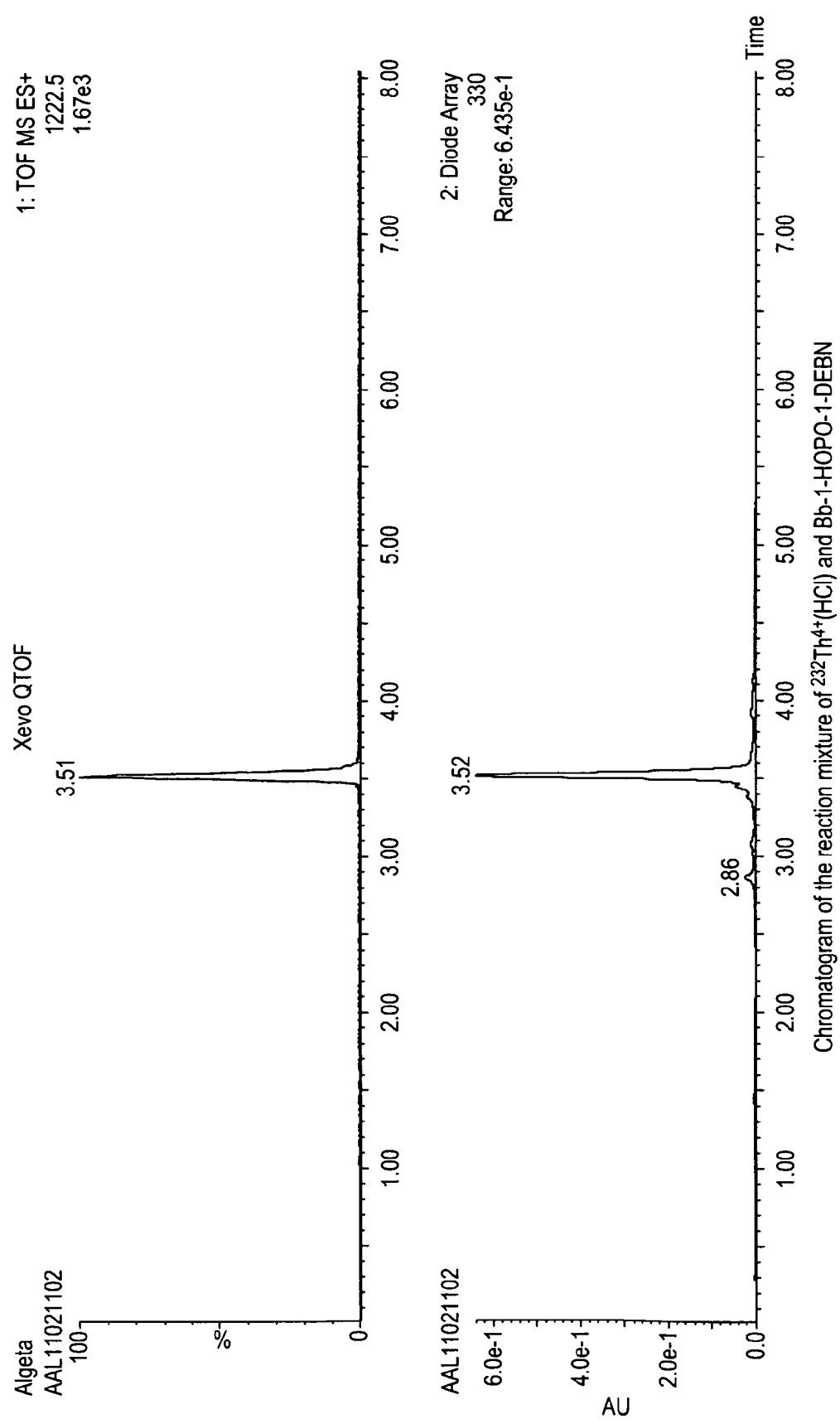
FIG. 15—shows the chromatogram of the reaction mixture of $^{232}Th^{4+}$ (HCl) and 1 mg/mL Bb-1-HOPO-1-DEBN (theoretical ratio 2:3) after 15 minutes at RT. There are significant amounts of the complex $^{232}$Th-Bb-1-HOPO-1-DEBN ($t_r$=3.52). Upper trace: Mass chromatogram of m/z 1222.5. Lower trace: UV at 330 nm.
Figure 16:
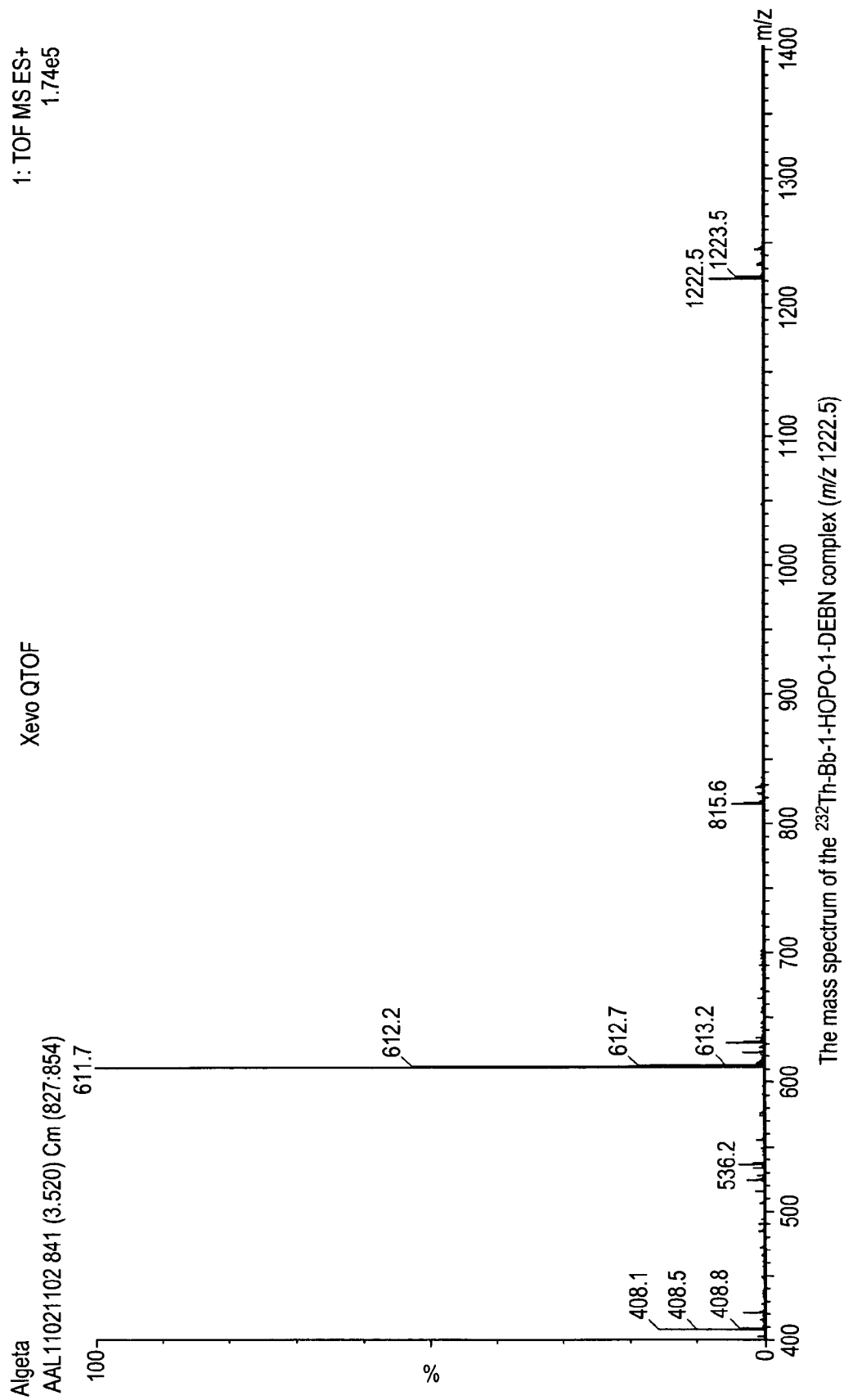
FIG. 16—shows the mass spectrum of the $^{232}$Th-Bb-1-HOPO-1-DEBN complex (m/z 1222.5).

A stock solution was prepared by dissolving Bb-1-HOPO-1-DEBN (made in Example 4) in DMSO (Biotech grade solvent 99.8%) to 1 mg/mL. A chelation experiment was conducted by mixing the 1 mg/mL solution with $^{232}$Th 0.01 M HCl (Perkin Elmer) as specified in Example 5. The LC-MS separation and analysis was performed as described in Example 6. The results showed that the expected $^{232}$Th-Bb-1-HOPO-1-DEBN complex was rapidly formed, FIGS. 15 and 16.

Example 8—Conjugation of ALG-DD-NCS to Trastuzumab, Labeling of the Conjugate with Thorium-227, and Confirming Retained Target Binding Conjugation Pharmaceutical grade of the monoclonal antibody trastuzumab (Herceptin®, Roche) was used. The antibody was buffer exchanged into 0.9% NaCl to a concentration of 6.3 mg/mL. A stock solution of ALG-DD-NCS was prepared in DMSO, containing 1 mg/mL (disregarding impurities). DMSO stock solution was added to the antibody solution corresponding to a chelator to antibody molar ratio of 6.5:1, or less. A 0.07 M borax solution was added to the reaction solution to give pH 9 following incubation at 37° C. over night. The resulting conjugate was purified and buffer exchanged on an Amicon Ultra-4 (30 k MWCO) centrifugal filter unit. Aliquots of 1 mg in 100 μL 0.9% NaCl were frozen and stored at −18° C. until use.

Labeling

100 μL 0.5 M NaOAc-buffer (pH 5.5) was added to one vial of 1 mg ALG-DD-NCS-trastuzumab conjugate to obtain a pH suitable for labeling. This solution was mixed with 4.2-16.4 MBq $^{227}$Th in 0.01 M HCl, and the pH was checked with pH paper. The Eppendorf tube cap was wrapped in aluminum foil and the tube was placed in a thermomixer at room temperature for 15 minutes with gentle mixing.

The tube was further incubated at room temperature for 5 minutes after adding 10 μL saturated DTPA in MF-H$_2$O, intended to capture remaining free thorium-227.

The result was purified on a NAP-5 column using PBS to elute the labeled ALG-DD-NCS-trastuzumab conjugate, leaving the majority of free radionuclides (thorium-227 and daughter nuclides) and DTPA-thorium chelate on the column.

The column and eluted fractions were measured on a HPGe-detector GEM(15) to determine reaction yields and specific activity of the product. The product fraction was sterile filtered and stored at 4° C. over night.

A second NAP-5 column purification of the product fraction was performed before use.

Determining the Immunoreactive Fraction

SK-OV-3 cells (ATCC) were cultured under standard conditions. Fixed SK-OV-3 cells were prepared and examined by flow cytometry before use to confirm the presence of HER2 on the surface (data not shown). Regular medium was prepared with McCoy's 5A medium (GIBCO) added 10% FBS (PAA) and 1% Pen/Strep (BioChrom). Incubation of cells were performed in a $CO_2$-incubator at 37° C. and 5% $CO_2$, using T25 (25 cm$^2$) and T75 (75 cm$^2$) cell flasks.

Each experiment was performed in duplicate. Fixed SK-OV-3 cells were suspended in PBS and transferred to Eppendorf tubes (10 million cells/tube). Non-conjugated trastuzumab (Herceptin®, 10 μL from the stock solution) was added to the two reference tubes, and the blocking reaction was conducted at 37° C. for 30 minutes. Equal amounts of $^{227}$Th-ALG-DD-NCS-trastuzumab (ca 500 cpm) were added to each tube, followed by incubation at 37° C. for 2.5 hours. The samples were diluted with PBS, followed by centrifugation and transfer of half of the supernatant to new Eppendorf tubes. All tubes were measured for 5 minutes on a Wizard gamma counter and the amount of thorium-227 determined by applying a $^{227}$Th-protocol.

The binding in % was calculated as: 100*[(P+½S)−(½S)]/[(P+½S)+(½S)], where P and S are the activities measured in the cell pellet and the supernatant, respectively. The calculation is performed on the un-blocked samples to obtain total binding (%) and the blocked samples to obtain unspecific binding (%), and the IRF is calculated as: IRF (%)=total binding (%)−unspecific binding (%).

The data from this quality control, summarized in Table 4, show that $^{227}$Th-ALG-DD-NCS-trastuzumab binds the target cells.

TABLE 4

Results for the quality control performed on $^{227}$Th-ALG-DD-NCS-trastuzumab batches A and B, subsequently used in Examples 9 and 10 respectively.

| | Yield (%)$^i$ | Recovery (%)$^{ii}$ | Specific activity (Bq/μg)$^{iii}$ | Average IRF (%)$^{iv}$ | Average total binding (%)$^{iv}$ | Average unspecific binding (%)$^{iv}$ |
|---|---|---|---|---|---|---|
| Batch A | 60 | 95 | 10 166 | 65 | 84 | 20 |
| Batch B | 64 | 92 | 2 700 | 60 | 74 | 15 |

$^i$Yield (%) is calculated after NAP-5 purification of the reaction mixture.
$^{ii}$Recovery (%) is calculated after a new NAP-5 purification of the product fraction.
$^{iii}$Specific activity (Bq/μg) is calculated using the amount of $^{227}$Th (Bq) found in the product fraction divided on the amount of ALG-DD-NCS-trastuzumab (μg) used in the reaction mixture.
$^{iv}$IRF is estimated according to standard procedures.

Example 9—In Vitro Stability and Efficacy Studies of Thorium-227 Labeled ALG-DD-NCS-Trastuzumab Assessment of Binding Over Time The stability of binding to SK-OV-3 cells was evaluated for the $^{227}$Th-ALG-DD-NCS-trastuzumab construct by measuring the amount of $^{227}$Th-activity associated with SK-OV-3 cell pellets over 7 days. The results were compared to data obtained after incubation with free $^{227}$Th.

Figure 17:
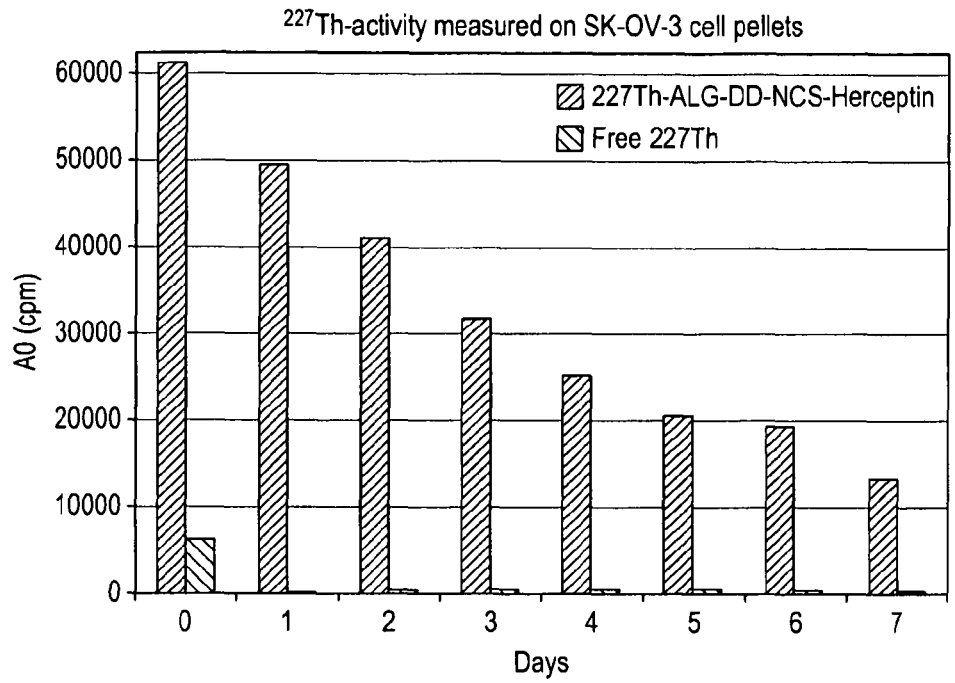
FIG. 17—shows the calculated amount of $^{227}$Th-ALG-DD-NCS-trastuzumab and free $^{227}$Th bound to SK-OV-3 cell pellets on day 0-7, shown as the decay corrected $^{227}$Th-activity (cpm).

SK-OV-3 cells were cultured as described in Example 8 were initially treated with 700 kBq $^{227}$Th-ALG-DD-NCS-trastuzumab or 700 kBq free $^{227}$Th, resulting in respectively 77 kBq (11%) and 7 kBq (1%)$^{227}$Th-activity on the cell pellet after 1 hour incubation (HPGe-detector GEM(50)). The $^{227}$Th-activity on SK-OV-3 cells was measured daily using the Wizard gamma counter ($^{227}$Th-protocol). The measured radioactivity was corrected for decay. The results presented in FIG. 17 show that only 20% of the activity remaining with the pellet after 1 hour is lost over the next 7 days. In contrast, the cells treated with free $^{227}$Th only bound a small fraction of the added activity, and lost most of it (ca 95%) during the following 24 hours. Thus, there is no specific binding of free $^{227}$Th to SK-OV-3 cells, whereas $^{227}$Th-ALG-DD-NCS-trastuzumab is efficiently retained.

Assessment of Cytotoxicity

The effect on tumor cell growth was investigated in two complementary assays. In the first experiment, the metabolic activity in cells was measured using a luminescent reagent binding to ATP molecules. Thus, a decreased luminescence signal indicates loss of metabolic activity. In the second experiment, the number of colonies formed was counted.

Luminescence was measured daily for 9 days, and the results from exposure to $^{227}$Th-ALG-DD-NCS-trastuzumab were compared to the luminescence of SK-OV-3 cells exposed to trastuzumab and free $^{227}$Th, respectively. SK-OV-3 cells growing in regular medium were used as control.

On day 0, 35 mL of 500 000 SK-OV-3 cells/mL in regular medium were transferred to 4 T75 cell flasks. These cell flasks were used to prepare the following sample solutions: (1) Regular medium, (2) 20 µg/mL trastuzumab, (3) 20 kBq/mL $^{227}$Th-ALG-DD-NCS-trastuzumab (10166 Bq/µg), (4) 20 kBq/mL free $^{227}$Th. The flasks were incubated in a $CO_2$-incubator for 1 hour. The supernatants were discarded, and the cells were trypsinized with 0.25% Trypsin-EDTA solution, washed with regular medium and centrifuged. Cell pellets were suspended in fresh regular medium and measured on a Wizard gamma counter ($^{227}$Th-protocol). Each incubation solution was distributed into 7 new T25 cell flasks, and incubated in a $CO_2$-incubator.

On days 1 and 2 the supernatants from one flask of each of the four sample solutions were discarded. The cell pellets were prepared as on day 0 and radioactivity measured on a Wizard gamma counter ($^{227}$Th-protocol) and on a HPGe-detector GEM(50). All samples were diluted 4-fold in regular medium, and 5×100 µL of each cell suspension were transferred into 5 wells of a View plate-96. Five wells were added 100 µL regular medium (without cells) for measurements of background luminescence. Finally, 100 µL of Cell Titer-Glo Reagent were added to each well, and the solutions were mixed on an orbital shaker to induce lysis. The luminescence signal was allowed to stabilize at room temperature for 10 minutes, then luminescence was measured three times on an Envision multiple plate reader, using the LUM-single program.

On day 3 cells were prepared and measurements on a Wizard gamma counter and Envision multiple plate reader, as described for day 1-2. Then, each cell suspension was diluted due to dense cell growth; ¾ cell suspension was transferred into a new T75 cell flask, added regular medium and incubated in a $CO_2$-incubator over night.

On each of days 4-9 the four T75 cell flasks were trypsinized with 0.25% Trypsin-EDTA solution, washed with regular medium and centrifuged. Cell pellets were diluted 4-fold in regular medium, and 100 µL portions taken out and measurements performed as above. Then, ¾ of the cell suspensions were diluted in regular medium, transferred into new T75 cell flasks and incubated in a $CO_2$-incubator over night.

Figure 18:
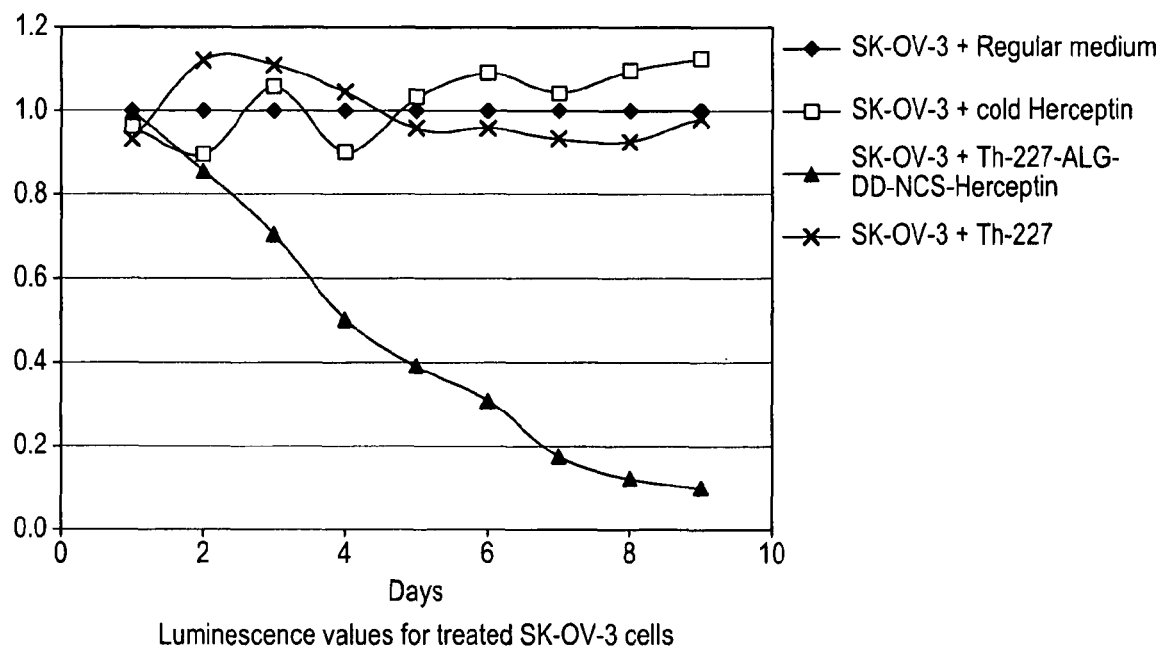
FIG. 18—shows normalized luminescence values for SK-OV-3 cells treated with (1) Regular medium (control); (2) 20 µg/mL trastuzumab; (3) 20 kBq/mL $^{227}$Th-ALG-DD-NCS-trastuzumab (10166 Bq/µg); and (4) 20 kBq/mL free $^{227}$Th.

FIG. 18 shows the luminescence measurements on SK-OV-3 cells treated with $^{227}$Th-ALG-DD-NCS-trastuzumab (10166 Bq/µg), trastuzumab and free $^{227}$Th, normalized to the luminescence values obtained for SK-OV-3 cells growing in regular medium (control). The luminescence signals for SK-OV-3 cells treated with $^{227}$Th-ALG-DD-NCS-trastuzumab decreased gradually from day 1 to day 9, while the other treatments showed almost constant luminescence signals and growth during this period. The metabolic activity of SK-OV-3 cells treated with $^{227}$Th-ALG-DD-NCS-trastuzumab decreased over time, and at day nine almost all cells were dead. This result indicates a significant and sustained cytotoxic effect of $^{227}$Th-ALG-DD-NCS-trastuzumab.

A clonogenic assay was performed to evaluate cell colony growth after exposing single cells to potentially cytotoxic conditions. SK-OV-3 cells were incubated in different concentrations of $^{227}$Th-ALG-DD-NCS-trastuzumab, trastuzumab or free $^{227}$Th for 1 hour, followed by incubation for 12 days to induce colony growth.

Preparation of cells was done as above, and in each sample 12000 cells in 5 mL regular medium was transferred into a T25 flask. The effect of 3 amounts of each reagent was investigated, for $^{227}$Th-ALG-DD-NCS-trastuzumab and $^{227}$Th, 5, 10 and 20 kBq/mL, and for trastuzumab 5, 10 and 20 µg/mL, (final concentrations) respectively. One control flask was prepared. All 10 T25 cell flasks were incubated in a $CO_2$-incubator for 1 hour. The supernatants were discarded, and the cells were washed with regular medium, trypsinized with 0.25% Trypsin-EDTA solution, washed with regular medium and centrifuged. Cell pellets were suspended in regular medium, and each of the ten cell suspensions were divided on 6 new T25 cell flasks; 3 cell flasks à 1000 cells and 3 cell flasks à 3000 cells. The resulting 60 T25 cell flasks were incubated in a $CO_2$-incubator until colonies reached a visible size (ca 50 cells/colony). After incubation for 12 days, the medium was removed. Cells were washed with PBS, fixed with ethanol, stained with 0.25% Trypan Blue in PBS, washed with tap water and finally dried at 45° C. over night. Colonies were counted manually, and the average number of colonies in each incubation solution was plotted graphically.

Figure 19:
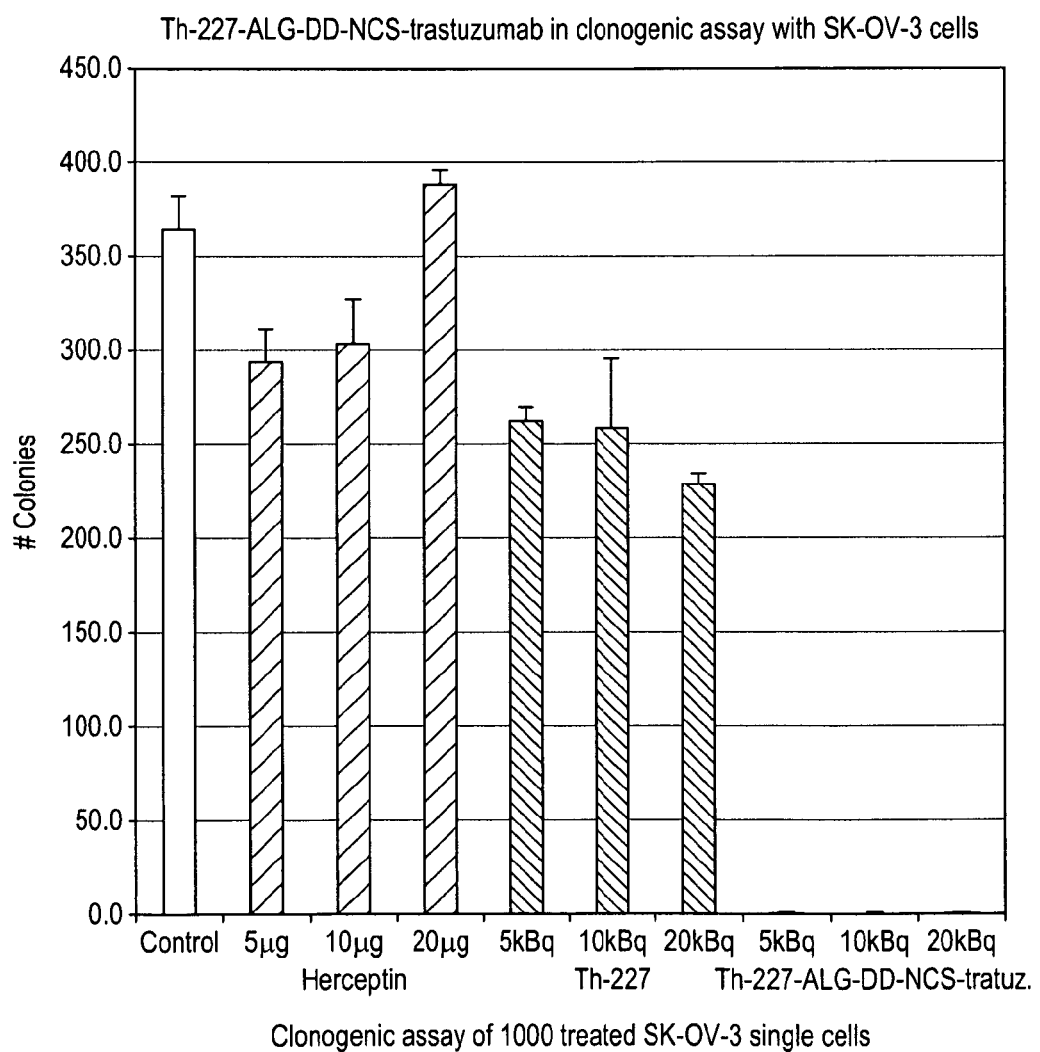
FIG. 19—shows a clonogenic assay of 1000 SK-OV-3 single cells treated with (1) Regular medium (control); (2) trastuzumab; (3) free $^{227}$Th; and (4)$^{227}$Th-ALG-DD-NCS-trastuzumab (10166 Bq/µg). (Mean±SD; n=3)
Figure 20:
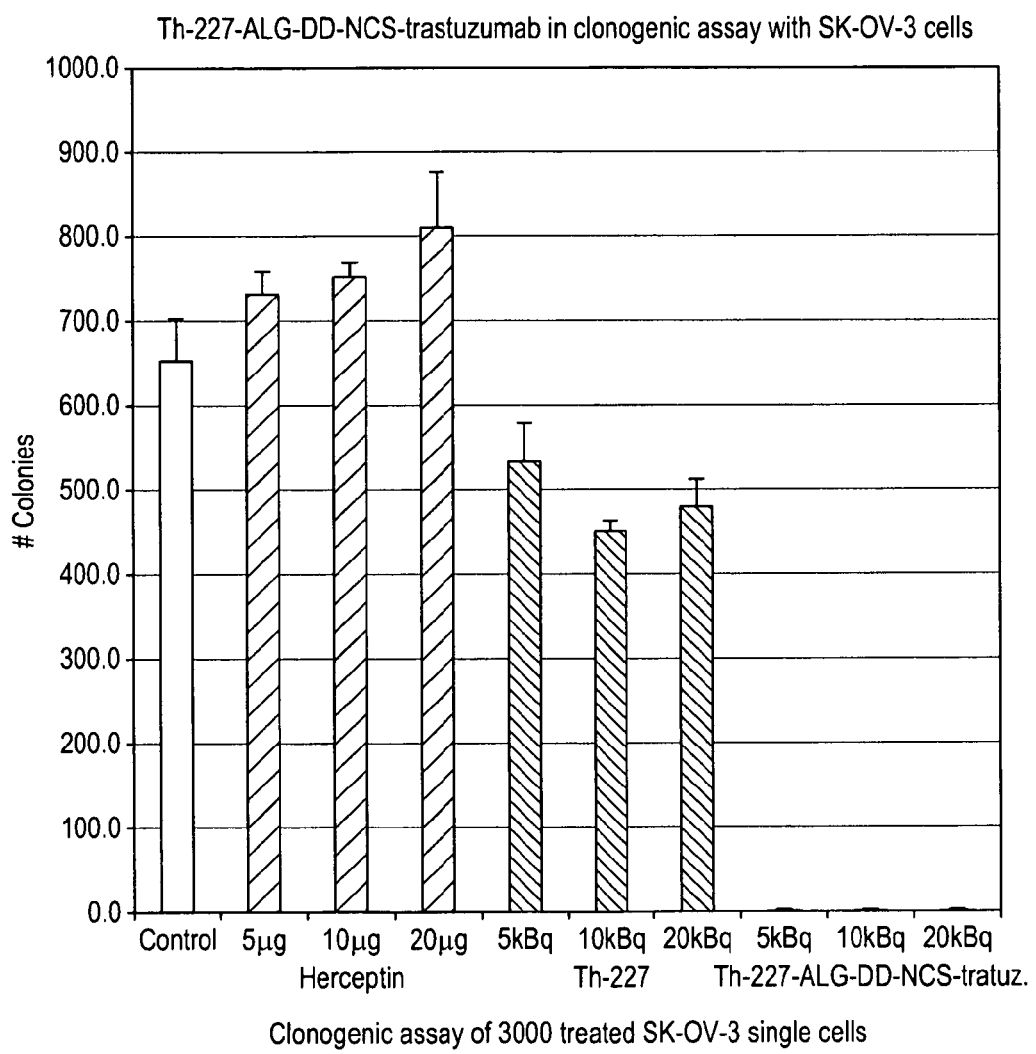
FIG. 20—shows a clonogenic assay of 3000 SK-OV-3 single cells treated with (1) Regular medium (control); (2) trastuzumab; (3) free $^{227}$Th; and (4)$^{227}$Th-ALG-DD-NCS-trastuzumab (10166 Bq/µg). (Mean±SD; n=3)

The results shown in FIGS. 19 and 20 show that 1 hour incubation with $^{227}$Th-ALG-DD-NCS-trastuzumab efficiently killed SK-OV-3 cells. Incubation with free $^{227}$Th might have had some cell killing effect, not apparent in the first cytotoxicity assay where a larger number of cells are used. Incubation with trastuzumab had no negative effect on cell growth.

Example 10—In Vivo Tumor Targeting of Thorium-227 Labeled ALG-DD-NCS-Trastuzumab 100 µL (15 kBq) of sterile filtered $^{227}$Th-ALG-DD-NCS-trastuzumab (2700 Bq/µg) was injected into the lateral tail vein of ten Balb/c nude mice bearing SK-OV-3 xenografts. Five mice were sacrificed after 24 hours and the other five after 4 days, and organs of interest were excised and weighed. All samples and 3 standard solutions containing 10% ID/g were measured for 5 minutes on a Wizard gamma counter ($^{227}$Th-protocol). The results were expressed as % injected dose per gram tissue (% ID/g).

Figure 21:
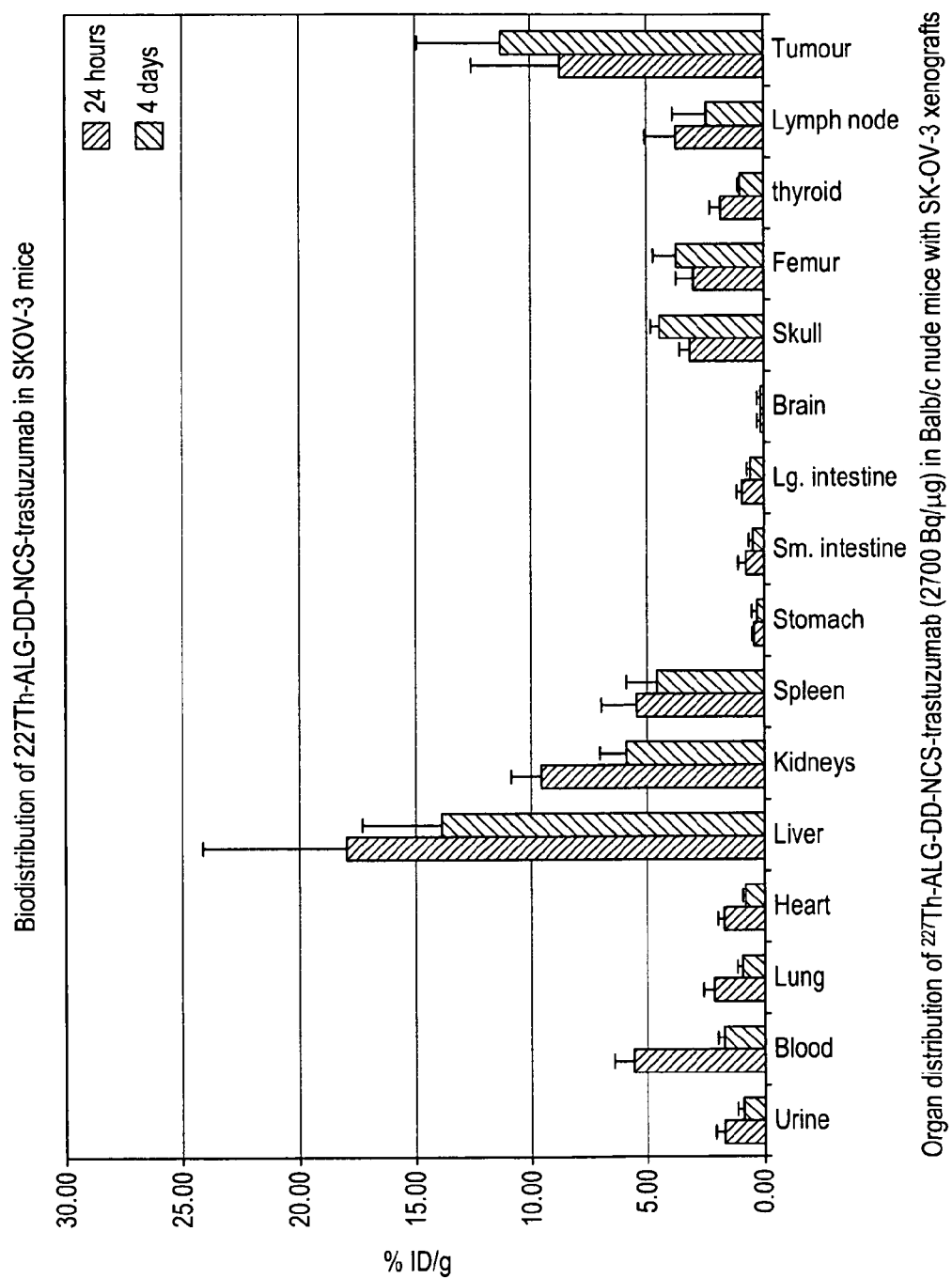
FIG. 21—shows the organ distribution of $^{227}$Th-ALG-DD-NCS-trastuzumab (2700 Bq/µg) in Balb/c nude mice with SK-OV-3 xenografts, after biodistribution for 24 hours and 4 days. (Mean±SD; n=5)

The results shown in FIG. 21 support that $^{227}$Th-ALG-DD-NCS-trastuzumab specifically binds to the tumor. The uptake values were moderate, but increased somewhat between 24 hours and 4 days uptake (from 8.7% ID/g to 11.3% ID/g), while the concentration in blood decreased to around 1% ID/g.

The uptake in skull and femur also increased somewhat between 24 hours and 4 days, but these values were generally low (2.8-3.2%, 24 h), indicating very little free $^{227}$Th circulating in the system, and thus suggesting a high degree of stability of the $^{227}$Th-ALG-DD-NCS-trastuzumab complex. Further support for this conclusion is lended by the high likelihood that a fraction of the activity measured in skull and femur is caused by uptake of the daughter nuclide [223]Ra. Some of this [223]Ra may be detected within the gated window specified for [227]Th-measurements on a Wizard gamma counter, hence the calculated % ID/g-values for skull and femur may be overestimates of the amount of [227]Th-ALG-DD-NCS-trastuzumab accumulated in these tissues.

Example 11—Preparation of a Chelating Moiety

Preparation of 3-benzyloxy-1-methyl-4-(2-thioxothiazolidin-1-yl)carbonyl-2(1H)-pyridinone (Structure A)

Step 1)—1-Methyl-3-hydroxy-2(1H)-pyridinone 3-hydroxy-2(1H)-pyridinone (34.44 g, 0.31 mol) and iodomethane (75 g, 0.53 mol) are placed in an 80 mL capped Teflon container, and heated to 150° C. for about 48-60 hours in a Parr bomb. The cooled bomb is opened and the excess iodomethane decanted. The resultant thick dark oil is mixed with sodium sulfite (64 g, 0.5 mol) and dissolved in 300 mL water to form a pale brown solution. The solution is neutralized to pH 7-8 and filtered to remove insoluble impurities. The filtrate is then extracted with methylene chloride (4×100 mL). The combined extracts are then dried, applied to a flash silica gel plug (6 cm.×8 cm) and eluted with 4% methanol in methylene chloride. The solvent is removed to give the title compound (24.3 g, 62.6%) as colourless crystals.

Step 2_-4-Carboxy-1-methyl-3-hydroxy-2(1H)-pyridinone

1-Methyl-3-hydroxy-2(1H)-pyridinone (1) (6.25 g, 50 mmol) is mixed with anhydrous potassium carbonate (36 g, 0.26 mol) and vacuum dried. The mixture is then heated to 175-185° C. for 3 days in a Parr bomb under dry carbon dioxide gas (850 psi). The cooled bomb is opened and the resultant pale yellow solid dissolved in iced water and acidified with 6N HCl to produce a beige crystalline product.

Step 3—3-Benzyloxy-4-carboxy-1-methyl-2(1H)-pyridinone

4-Carboxy-1-methyl-3-hydroxy-2(1H)-pyridinone (6.8 g, 0.04 mol) is mixed with benzyl chloride (12.1 g, 0.088 mol) and anhydrous potassium carbonate (13.8 g, 0.1 mol) in anhydrous dimethyl-formamide (DMF) (120 mL). The mixture is heated in darkness under nitrogen to 75-80° C. for 16 hours. The resulting mixture is then filtered and the solvent evaporated to yield a dark oil. The oil is purified by application to a silica gel plug (6 cm.×8 cm) and elution with 4% methanol in methylene chloride resulting in 3-benzyloxy-4-benzyloxycarbonyl-1-methyl-2(1H)-pyridinone as a pale yellow, thick oil. This is taken up in methanol (50 mL) and a 6M NaOH solution (10 mL), and the mixture stirred at room temperature for 4 hours, followed by evaporation to dryness. The residue is dissolved in water (100 mL), and acidified with 6M HCl solution to pH 2 to give the title compound (9.3 g 88.7%), as a white crystalline product.

Step 4—3-benzyloxy-1-methyl-4-(2-thioxothiazolidin-1-yl)carbonyl-2(1H)-pyridinone To a solution of 3-benzyloxy-4-carboxy-1-methyl-2(1H)-pyridinone (1.05 g, 4 mmol), 2-mercaptothiazoline (0.50 g, 4.2 mmol) and a catalytic amount of 4-dimethylaminopyridine (DMAP) in dry dichloromethane (50 mL), is added N,N'-dicyclohexylcarbodiimide (DCC) (0.86 g, 4.2 mmol). Alter stirring for 4 hours, the dicyclohexylurea (DCU) solids are removed by filtration. The yellow filtrate is then rotary evaporated to provide a yellow solid. Crystallization from isopropanol-methylene chloride gives the title compound (Structure A, 1.16 g, 80.4%) as bright yellow crystalline plates.

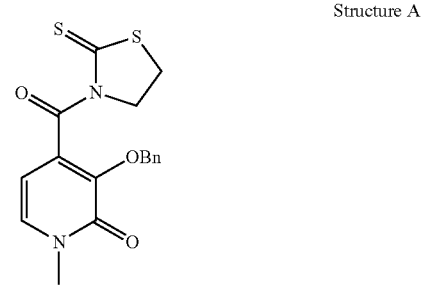 [SMILES: Cn1ccc(C(=O)N2CCSC2=S)c(OCc2ccccc2)c1=O]

Structure A

Example 12—Preparation of 3,2-HOPO Precursor for Formula VIII

Preparation of the cyclic salt (Structure 5) is done according to the following scheme:

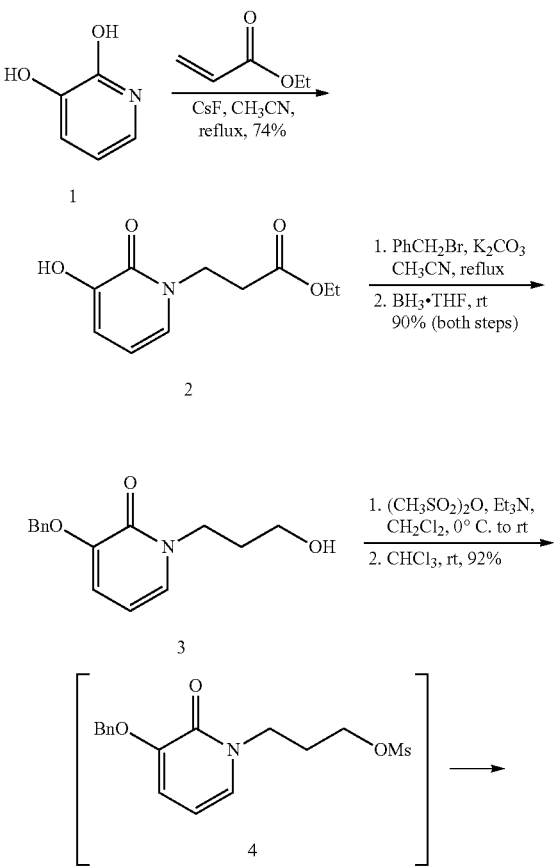

-continued

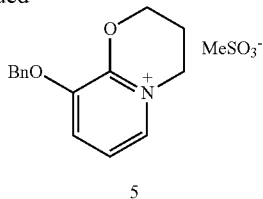
5

The cesium fluoride (10 mol %) assisted Michael reaction of 2,3-dihydroxypyridine (2,3-DHP) 1 with ethyl acrylate in refluxing acetonitrile gave the corresponding ester 2 in good yields. Subsequent O-benzylation of 2 using standard conditions K2CO3/acetonitrile/reflux) followed by reduction of the ester moiety (BH3.THF, rt) gave alcohol 3 in 90% yield after chromatography. Treatment of the alcohol 3 with methanesulfonic anhydride in dichloromethane in the presence of triethylamine led directly to the formation of the desired cyclic salt 5 (~85-90%) along with some of the intermediate mesylate 4 (~10-15%), as determined by $^1$H NMR spectral analysis. Complete conversion to the cyclic salt 5 could be achieved by stirring the crude product mixture from the mesylation in chloroform at room temperature. After trituration with hot ethyl acetate, the salt 5 was isolated as a pale white solid in 92% yield in high purity.

Example 13—Preparation of Compound of Formula VIII

Salt 5 (0.2 g) is added to 1.2 equivalents of cyclene (1,4,7,10-tetraazacyclododecane) in the presence of triethylamine in acetonitrile (3 ml) and heated at 60° C. for 2 days under nitrogen. The reaction is then diluted with dichloromethane (50 ml) and washed with saturated NaHCO$_3$ (50 ml). The aqueous layer is extracted once more with dichloromethane (25 ml). The combined organic extracts is dried with sodium sulphate, the solvent is removed in vacuo and the excess N-methylbenzylamine is removed via vacuum distillation to give VIII.

Example 14—Preparation of Compound of Formula IX

To a solution of 3-benzyloxy-1-methyl-4-(2-thioxothiazolidin-1-yl)carbonyl-2(1H)-pyridinone in methylene chloride the corresponding functionalized N,N,N',N'-tetrakis(2-aminoethyl)ethylenediamine (Structure B, Z being a protecting group) will be added. After stirring for four hours, the mixture is filtered and taken to dryness.

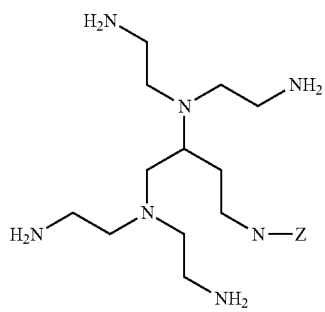
Structure B

The appropriate benzyl-protected precursor product will be isolated from the reaction mixture on a flash silica column with propanol in methylene chloride. The final product with structure IX will be available after acidic deprotection of the hydroxyl groups.

Example 15

Structure VIII will be conjugated to a targeting molecule using standard methods to those skilled in the art. For example will the N-hydroxysuccinimide (NHS) ester be prepared and conjugated to proteins and peptides using standard conditions and the resulting conjugated protein will be isolated using gel filtration.

Example 16

Thorium-227 Labeling of the Conjugated Protein

A 10 mg/mL solution of the conjugated protein (having an octadentate ligand attached by means of a coupling moiety) will be made in a suitable buffer solution, eg. 0.5 M NaOAc-buffer (pH 5.5), and labeled with purified thorium-227 at 25° C. for 1 h followed by a purification step on a gel filtration column.

The invention claimed is:

1. A tissue-targeting complex consisting of:
    a tissue targeting moiety selected from the group consisting of an antibody, an antibody construct, a fragment of an antibody, a construct of fragments of antibodies, a peptide, an amino acid, a steroidal hormone, a non-steroidal hormone, a folate, an estrogen, a testosterone, a biotin, and a mixture thereof;
    an octadentate hydroxypyridinone-containing ligand; and
    an ion of an alpha-emitting 227-thorium radionuclide,
    wherein said octadentate ligand is selected from the group consisting of

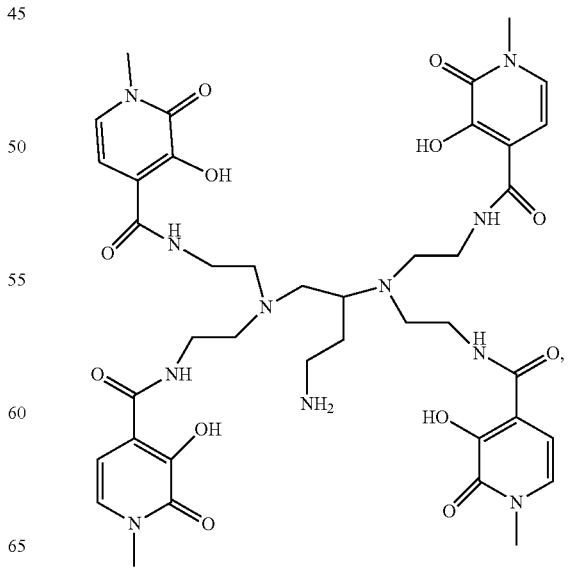

41
-continued
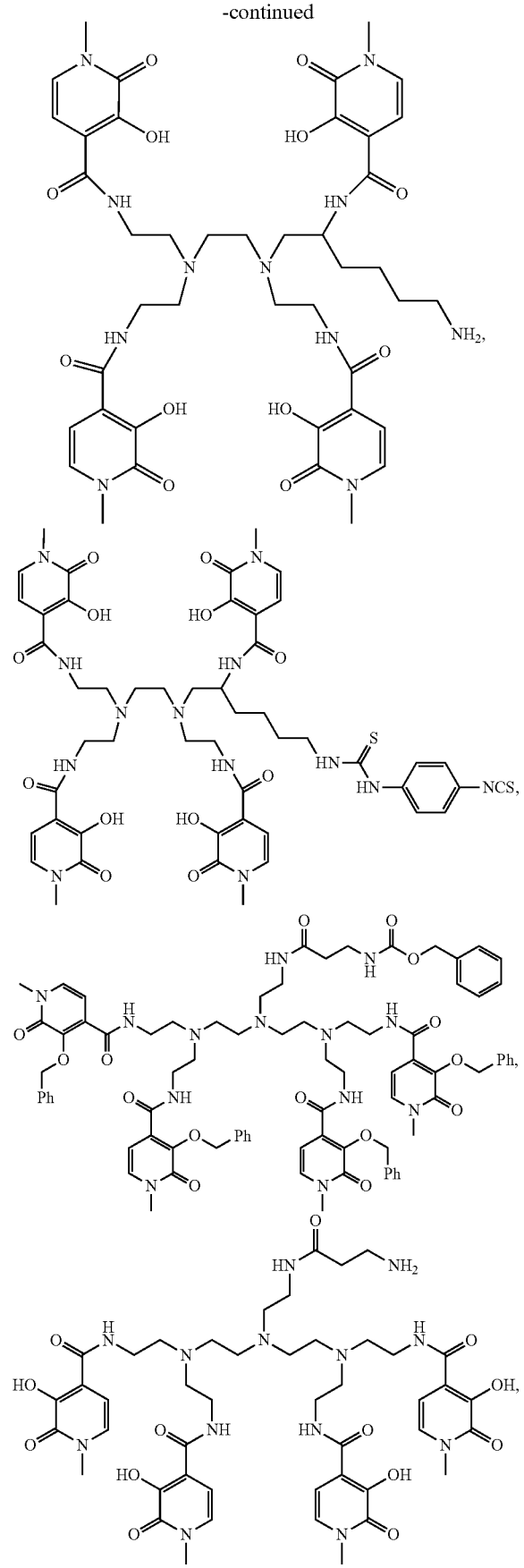
42
-continued
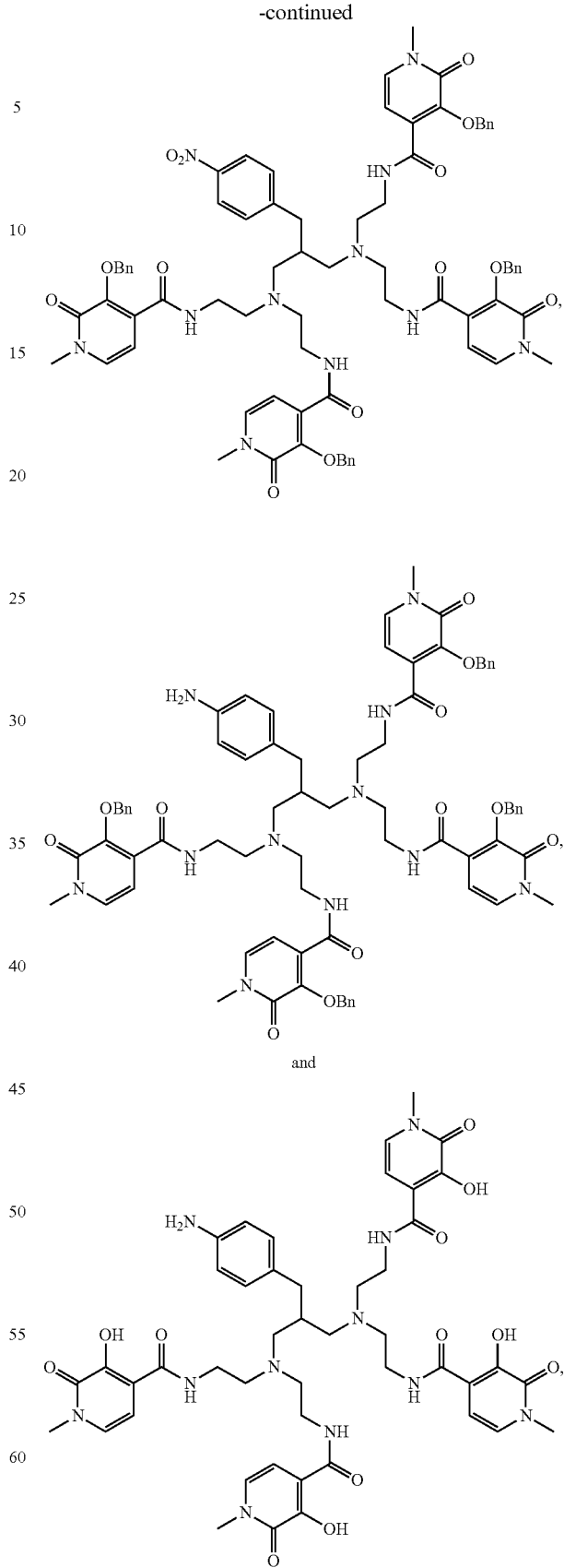
wherein Bn is a benzyl group.

2. A method of treatment of a human or non-human animal body having a hyperplastic or a neoplastic disease, comprising administering at least one tissue-targeting complex to said human or non-human animal body, wherein said tissue-targeting complex is the tissue-targeting complex of claim 1, wherein said hyperplastic or neoplastic disease is selected from the group consisting of a carcinoma, a sarcoma, a myeloma, a leukemia, a lymphoma and a mixed type cancer.

3. A pharmaceutical composition comprising a tissue-targeting complex together with at least one pharmaceutical carrier or excipient, wherein said tissue-targeting complex is the tissue-targeting complex of claim 1.

4. A kit comprising the tissue targeting complex of claim 1.

* * * * *